(12) United States Patent
Kokubo et al.

(10) Patent No.: US 12,186,112 B2
(45) Date of Patent: Jan. 7, 2025

(54) BLOOD PRESSURE-RELATED DISPLAY DEVICE, BLOOD PRESSURE-RELATED INFORMATION DISPLAY METHOD, AND COMPUTER-READABLE RECORDING MEDIUM

(71) Applicants: OMRON HEALTHCARE CO., LTD., Muko (JP); JICHI MEDICAL UNIVERSITY, Tokyo (JP)

(72) Inventors: Ayako Kokubo, Kyoto (JP); Mitsuo Kuwabara, Kyoto (JP); Shingo Yamashita, Kyoto (JP); Kazuomi Kario, Tochigi (JP)

(73) Assignees: OMRON HEALTHCARE CO., LTD., Muko (JP); JICHI MEDICAL UNIVERSITY, Tokyo (JP)

( * ) Notice: Subject to any disclaimer, the term of this patent is extended or adjusted under 35 U.S.C. 154(b) by 684 days.

(21) Appl. No.: 17/482,297

(22) Filed: Sep. 22, 2021

(65) Prior Publication Data
US 2022/0008023 A1   Jan. 13, 2022

Related U.S. Application Data

(63) Continuation of application No. PCT/JP2020/008982, filed on Mar. 3, 2020.

(30) Foreign Application Priority Data

Mar. 25, 2019   (JP) ................ 2019-056995

(51) Int. Cl.
*A61B 5/021*   (2006.01)
*A61B 5/00*   (2006.01)
(Continued)

(52) U.S. Cl.
CPC .......... *A61B 5/743* (2013.01); *A61B 5/02116* (2013.01); *G06T 11/001* (2013.01); *G06T 11/206* (2013.01); *G06T 2210/41* (2013.01)

(58) Field of Classification Search
None
See application file for complete search history.

(56) References Cited

U.S. PATENT DOCUMENTS

2018/0110462 A1\*   4/2018   Asvadi ................ A61B 5/0205
2018/0256050 A1\*   9/2018   Kuwabara ............. G16H 15/00
(Continued)

FOREIGN PATENT DOCUMENTS

CN   107624049 A   1/2018
CN   108135511 A   6/2018
(Continued)

OTHER PUBLICATIONS

Mangiafico, S.S. "Basic Plots," in Summary and Analysis of Extension Program Evaluation in R, version 1.15.0. 2016. https://web.archive.org/web/20181225112054/https://rcompanion.org/handbook/C_04.html (Year: 2016).\*

(Continued)

*Primary Examiner* — Meredith Weare
(74) *Attorney, Agent, or Firm* — Oliff PLC

(57) ABSTRACT

According to the present invention, blood pressure surges is detected from time-series data on blood pressure of a subject that varies with pulsation based on predetermined determination criteria. A feature amount indicating a characteristic of each blood pressure surge thus detected is obtained. Statistical processing is performed on an occurrence number of the blood pressure surges thus detected and/or the feature amount to obtain a statistical amount for each of time slots. A required attention degree indicating a level of attention being required to the blood pressure surge is obtained for (Continued)

each of the time slots based on the statistical amount of the occurrence number of the blood pressure surges and/or the feature amount. The required attention degree thus obtained and/or the statistical amount are displayed side by side for each of the time slots on a display screen.

11 Claims, 14 Drawing Sheets

(51) Int. Cl.
  *G06T 11/00* (2006.01)
  *G06T 11/20* (2006.01)

(56) References Cited

U.S. PATENT DOCUMENTS

| | | | | |
|---|---|---|---|---|
| 2019/0374169 A1* | 12/2019 | Inoue | .................... | A61B 8/468 |
| 2019/0387979 A1* | 12/2019 | Kokubo | ............... | A61B 5/7264 |
| 2019/0388037 A1* | 12/2019 | Kokubo | ............... | A61B 5/6824 |

FOREIGN PATENT DOCUMENTS

| | | |
|---|---|---|
| JP | 2016-202346 A | 12/2016 |
| JP | 2018-149173 A | 9/2018 |
| JP | 2018-149183 A | 9/2018 |
| JP | 2018-153269 A | 10/2018 |
| WO | 2017/082107 A1 | 5/2017 |
| WO | 2018/002995 A1 | 1/2018 |

OTHER PUBLICATIONS

Dunn, Kevin. "Visualizing Process Data," in Process Improvement Using Data. Jan. 28, 2016. (Year: 2016).*
"Excel 2016: Conditional Formatting." GCFGlobal. Retrieved Jun. 15, 2024. https://edu.gcfglobal.org/en/excel2016/conditional-formatting/1/ (Year: 2016).*
English machine translation of JP-2018153269-A. Retrieved Jun. 15, 2024. (Year: 2024).*
English machine translation of JP-2018149173-A. Retrieved Jun. 15, 2024. (Year: 2024).*
English machine translation of CN-108135511-A. Retrieved Jun. 15, 2024. (Year: 2024).*
English machine translation of CN-107624049-A. Retrieved Jun. 15, 2024. (Year: 2024).*
Dec. 26, 2023 Office Action issued in Chinese Patent Application No. 202080024256.X.
May 12, 2020 International Search Report issued in International Patent Application No. PCT/JP2020/008982.

* cited by examiner

Fig.8

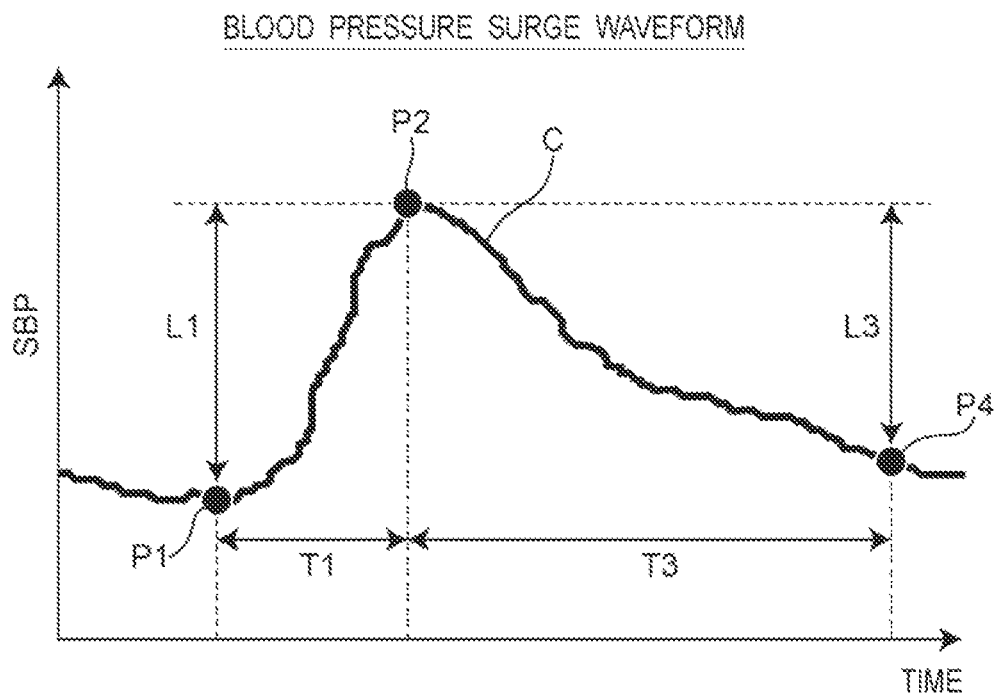

Fig.9

| INDIVIDUAL INDEX | LEVEL | | |
|---|---|---|---|
| | LOW | MEDIUM | HIGH |
| OCCURRENCE NUMBER | EQUAL TO OR LESS THAN 10 TIMES | GREATER THAN 10 TIMES AND EQUAL TO OR LESS THAN 30 TIMES | GREATER THAN 30 TIMES |
| VARIATION AMOUNT | EQUAL TO OR LESS THAN 25 mmHg | GREATER THAN 25 mmHg AND EQUAL TO OR LESS THAN 30 mmHg | GREATER THAN 30 mmHg |
| PEAK VALUE | EQUAL TO OR LESS THAN 120 mmHg | GREATER THAN 120 mmHg AND EQUAL TO OR LESS THAN 150 mmHg | GREATER THAN 150 mmHg |

Fig.10

| TIME SLOT | SURGE OCCURRENCE NUMBER [TIMES] | OCCURRENCE NUMBER INDEX | MEAN SURGE VARIATION AMOUNT [mmHg] | VARIATION AMOUNT INDEX | MEAN SURGE PEAK VALUE [mmHg] | PEAK VALUE INDEX | ... | REQUIRED ATTENTION DEGREE |
|---|---|---|---|---|---|---|---|---|
| 10 PM RANGE | 3 | LOW | 22 | LOW | 141 | MEDIUM | ... | LOW |
| 11 PM RANGE | 11 | MEDIUM | 25 | MEDIUM | 143 | MEDIUM | | MEDIUM |
| 0 AM RANGE | 14 | MEDIUM | 27 | MEDIUM | 149 | MEDIUM | | MEDIUM |
| 1 AM RANGE | 25 | MEDIUM | 31 | HIGH | 151 | HIGH | | HIGH |
| 2 AM RANGE | 23 | MEDIUM | 28 | MEDIUM | 153 | HIGH | | MEDIUM |
| 3 AM RANGE | 20 | MEDIUM | 22 | LOW | 144 | MEDIUM | | MEDIUM |
| 4 AM RANGE | 21 | MEDIUM | 24 | LOW | 146 | MEDIUM | | MEDIUM |
| 5 AM RANGE | 14 | MEDIUM | 20 | LOW | 145 | MEDIUM | | MEDIUM |
| 6 AM RANGE | 7 | LOW | 21 | LOW | 147 | MEDIUM | | LOW |
| 7 AM RANGE | 1 | LOW | 21 | LOW | 149 | MEDIUM | | LOW |

Fig. 14

| PATIENT NUMBER | SURGE OCCURRENCE NUMBER [TIMES] | MEAN SURGE VARIATION AMOUNT [mmHg] | MEAN SURGE PEAK VALUE [mmHg] | MEAN SURGE RISING SPEED [mmHg/sec] | MEAN SURGE FALLING TIME [sec] | ... | REQUIRED ATTENTION DEGREE |
|---|---|---|---|---|---|---|---|
| PATIENT A | 14 | 27 | 149 | 1.3 | 15 | | MEDIUM |
| PATIENT B | 20 | 22 | 144 | 1.6 | 17 | | MEDIUM |
| PATIENT C | 1 | 21 | 149 | 0.8 | 5 | | LOW |
| PATIENT D | 7 | 21 | 147 | 0.9 | 9 | | LOW |
| PATIENT E | 25 | 31 | 158 | 2.1 | 21 | | HIGH |
| PATIENT F | 21 | 24 | 146 | 1.4 | 13 | | MEDIUM |
| ... | | | | | | | |

BLOOD PRESSURE-RELATED DISPLAY DEVICE, BLOOD PRESSURE-RELATED INFORMATION DISPLAY METHOD, AND COMPUTER-READABLE RECORDING MEDIUM

CROSS-REFERENCE TO RELATED APPLICATION

This application is based on an application No. 2019-056995 filed in Japan on Mar. 25, 2019, the entire content of which is hereby incorporated by reference.

TECHNICAL FIELD

The present invention relates to a blood pressure-related information display device and a blood pressure-related information display method, and more particularly to a device and method for displaying information on a blood pressure surge of a subject in a visualized form. The present invention further relates to a computer-readable recording medium storing a program for causing a computer to execute the blood pressure-related information display method.

BACKGROUND ART

It is known that, when a patient suffering from sleep apnea syndrome (SAS) resumes breathing after apnea, the blood pressure rises over, for example, about 5 seconds to 15 seconds and then falls. Herein, such a rapid blood pressure variation is referred to as a "blood pressure surge" (or simply a "surge").

In the related art, for example, Patent Literature 1 (WO 2017/082107 A1) discloses a relationship between frequency of variations (blood pressure surges) [times/hour] and a representative value of surge variation amounts (differences between a blood pressure value at a surge start point and a blood pressure value at a surge peak point) [mmHg] for a patient suffering from sleep apnea syndrome (SAS) is displayed in a two-dimensional graph form. Displaying information on the blood pressure surge occurring in the patient in a visualized form is considered to be useful for diagnosis and treatment of SAS.

SUMMARY OF INVENTION

From a study under 24 hour ambulatory blood pressure monitoring (ABPM), where blood pressure is measured at several points per hour (this is referred to as "spot measurement"), it is known that blood pressure variations during the night are related to a risk of a cardiovascular event (angina pectoris, myocardial infarction, ischemic heart failure, or the like). It is therefore considered clinically important to display, in a visualized form, information on the blood pressure surge such as occurrence number of blood pressure surges, a surge peak value, a surge variation amount, and a risk evaluated based on such values for each time slot for blood pressure surges during the night.

Patent Literature 1, however, does not disclose that information on the blood pressure surge is displayed in a visualized form for each time slot.

Note that a blood pressure surge itself cannot be observed sufficiently under the spot measurement under ABPM. That is, for example, as illustrated in FIG. 16A, when blood pressure surges BS1, BS2, BS3, . . . sometimes occur, and a blood pressure baseline (line assumed to be a level of a blood pressure value in a period during which no blood pressure surge occurs) is above a blood pressure standard value LM (=135 mmHg), the risk evaluation can be made to some extent from the viewpoint of the absolute value of the blood pressure even under the spot measurement (measurement points are indicated by black dots "●" in FIGS. 16A and 16B). However, as illustrated in FIG. 16B, when blood pressure surges BS11, BS12, BS13, . . . sometimes occur, and the blood pressure baseline is below the blood pressure standard value LM, a blood pressure measurement value is substantially less than the blood pressure standard value LM (normal range) under the spot measurement although the blood pressure sometimes exceeds the blood pressure standard value LM due to the blood pressure surges BS11, BS12, BS13, . . . , and thus it is determined that there is no risk from the viewpoint of the absolute value of the blood pressure.

It is therefore an object of the present invention to provide a blood pressure-related information display device and a blood pressure-related information display method that allow information on the blood pressure surge to be displayed in a visualized form for each time slot. It is another object of the present invention to provide a computer-readable recording medium storing a program for causing a computer to execute the blood pressure-related information display method.

In order to achieve the above object, a blood pressure-related information display device according to the present disclosure is a blood pressure-related information display device that displays information on a blood pressure surge in a visualized form, the blood pressure-related information display device comprising:

a blood pressure surge detection part configured to detect, based on predetermined determination criteria, blood pressure surges from time-series data on blood pressure of a subject that varies with pulsation;

a feature amount calculation part configured to obtain a feature amount indicating a characteristic of each blood pressure surge detected;

a statistical amount calculation part configured to perform statistical processing on an occurrence number of the blood pressure surges detected and/or the feature amount to obtain a statistical amount for each of time slots, the statistical amount including at least the occurrence number of the blood pressure surges, a surge variation amount serving as the feature amount, and a surge peak value serving as the feature amount;

a required attention degree calculation part configured to obtain, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the time slots; and a display processing part configured to display, for each of the time slots, the required attention degree obtained and/or the statistical amount side by side on a display screen, wherein the required attention degree calculation part includes, when m is a natural number equal to or greater than two, an individual index calculation part configured to obtain, for each of the time slots, individual indexes indicating a level of attention being required to each statistical amount for the occurrence number of the blood pressure surges, the surge variation amount serving as the feature amount, and the surge peak value serving as the feature amount as one of m levels according to the level of attention being required based on a result of comparison with respective (m−1) predetermined thresholds different in magnitude, and an integration processing part configured to obtain, for each of the time slots, the required attention degree as one of the m levels by using the individual indexes obtained for each of the occurrence number of the blood pressure surges, the surge variation amount serving as the feature amount, and the surge peak value serving as the feature amount.

As used herein, the "predetermined determination criteria" typically refer to criteria for detection of a blood pressure surge of a patient suffering from sleep apnea syndrome (SAS). For example, as disclosed in Japanese Patent Application No. 2017-048946 and Japanese Patent Application No. 2017-050066, the "predetermined determination criteria" refer to that a range from a surge start point to a surge peak point falls within a peak detection section (for example, a period of 15 pulses), that a difference (blood pressure variation) between a systolic blood pressure value at the surge start point and a systolic blood pressure value at the peak point is equal to or greater than 20 mmHg (or 15 mmHg), that a period between the surge start point and the peak point is longer than a period of five pulses, and that a period between the peak point and a surge end point is longer than a period of seven pulses.

Further, the "feature amount" indicating a characteristic of a blood pressure surge refers to, for example, a surge peak value (blood pressure value at the peak point), a surge variation amount (difference in blood pressure value between the start point of the blood pressure surge and the peak point of the blood pressure surge), a surge time (time between the start point of the blood pressure surge and the end point of the blood pressure surge), a surge rising speed (value obtained by dividing the surge variation amount by the time between the start point of the blood pressure surge and the peak point of the blood pressure surge), or the like of the systolic blood pressure.

Further, the "statistical processing" refers to processing of averaging, processing of obtaining a median value, processing of obtaining a standard deviation, or the like.

Further, the "display screen" typically refers to a screen of a display device, but may be, for example, a paper surface output by a printer.

In another aspect, a blood pressure-related information display method according to the present disclosure is a blood pressure-related information display device method by which information on a blood pressure surge is displayed in a visualized form, the blood pressure-related information display device method comprising steps of:

detecting, based on predetermined determination criteria, blood pressure surges from time-series data on blood pressure of a subject that varies with pulsation;

obtaining a feature amount indicating a characteristic of each blood pressure surge detected;

performing statistical processing on an occurrence number of the blood pressure surges detected and/or the feature amount to obtain a statistical amount for each of time slots, the statistical amount including at least the occurrence number of the blood pressure surges, a surge variation amount serving as the feature amount, and a surge peak value serving as the feature amount;

obtaining, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the time slots; and displaying, for each of the time slots, the required attention degree obtained and/or the statistical amount side by side on a display screen, wherein the step of obtaining a required attention degree includes, when m is a natural number equal to or greater than two, obtaining, for each of the time slots, individual indexes indicating a level of attention being required to each statistical amount for the occurrence number of the blood pressure surges, the surge variation amount serving as the feature amount, and the surge peak value serving as the feature amount as one of m levels according to the level of attention being required based on a result of comparison with respective (m−1) predetermined thresholds different in magnitude, and obtaining, for each of the time slots, the required attention degree as one of the m levels by using the individual indexes obtained for each of the occurrence number of the blood pressure surges, the surge variation amount serving as the feature amount, and the surge peak value serving as the feature amount.

In another aspect, a blood pressure-related information display device that displays information on a blood pressure surge in a visualized form, the blood pressure-related information display device comprising:

a blood pressure surge detection part configured to detect, based on predetermined determination criteria, blood pressure surges from time-series data on blood pressure of a subject that varies with pulsation;

a feature amount calculation part configured to obtain a feature amount indicating a characteristic of each blood pressure surge detected;

a statistical amount calculation part configured to perform statistical processing on an occurrence number of the blood pressure surges detected and/or the feature amount for a plurality of subjects to obtain a statistical amount for each of the subjects, the statistical amount including at least the occurrence number of the blood pressure surges, a surge variation amount serving as the feature amount, and a surge peak value serving as the feature amount;

a required attention degree calculation part configured to obtain, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the subjects; and a display processing part configured to display, for each of the subjects, the required attention degree obtained and/or the statistical amount side by side on a display screen, wherein the required attention degree calculation part includes, when m is a natural number equal to or greater than two, an individual index calculation part configured to obtain, for each of the subjects, individual indexes indicating a level of attention being required to each statistical amount for the occurrence number of the blood pressure surges, the surge variation amount serving as the feature amount, and the surge peak value serving as the feature amount as one of m levels according to the level of attention being required based on a result of comparison with respective (m−1) predetermined thresholds different in magnitude, and an integration processing part configured to obtain, for each of the subjects, the required attention degree as one of the m levels by using the individual indexes obtained for each of the occurrence number of the blood pressure surges, the surge variation amount serving as the feature amount, and the surge peak value serving as the feature amount.

In another aspect, a blood pressure-related information display method according to the present disclosure is a blood pressure-related information display method by which information on a blood pressure surge is displayed in a visualized form, the blood pressure-related information display method comprising steps of:

detecting, based on predetermined determination criteria, blood pressure surges from time-series data on blood pressure of a subject that varies with pulsation;

obtaining a feature amount indicating a characteristic of each blood pressure surge detected;

performing statistical processing on an occurrence number of the blood pressure surges detected and/or the feature amount for a plurality of subjects to obtain a statistical amount for each of the subjects, the statistical amount including at least the occurrence number of the blood pressure surges, a surge variation amount serving as the feature amount, and a surge peak value serving as the feature amount;

obtaining, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the subjects; and displaying, for each of the subjects, the required attention degree obtained and/or the statistical amount side by side on a display screen, wherein the step of obtaining a required attention degree includes, when m is a natural number equal to or greater than two, obtaining, for each of the subjects, individual indexes indicating a level of attention being required to each statistical amount for the occurrence number of the blood pressure surges, the surge variation amount serving as the feature amount, and the surge peak value serving as the feature amount as one of m levels according to the level of attention being required based on a result of comparison with respective (m−1) predetermined thresholds different in magnitude, and obtaining, for each of the subjects, the required attention degree as one of the m levels by using the individual indexes obtained for each of the occurrence number of the blood pressure surges, the surge variation amount serving as the feature amount, and the surge peak value serving as the feature amount.

In yet another aspect, a computer-readable recording medium according to the present disclosure is a computer-readable recording medium non-transitorily storing a program for causing a computer to execute the above blood pressure-related information display method.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 8 is a diagram illustrating a waveform of a blood pressure surge.

FIG. 9 illustrates a criteria table for use in determining, as one of three levels of low, medium, and high, individual indexes indicating a level of attention being required to each of statistical amounts including an occurrence number of the blood pressure surges, a surge variation amount serving as a feature amount, and a surge peak value serving as the feature amount.

FIG. 10 is a diagram illustrating an example of a time slot table where three statistical amounts ("surge occurrence number", "mean surge variation amount", and "mean surge peak value") obtained for each time slot, three individual indexes ("occurrence number index", "variation amount index", and "peak value index") each indicating a level of attention being required to a corresponding one of the three statistical amounts, and a "required attention degree" obtained as a result of integrating the individual indexes are recorded in association with each other for each time slot.

FIG. 14 is a diagram illustrating an example of a patient-by-patient table where five obtained statistical amounts ("surge occurrence number", "mean surge variation amount", "mean surge peak value", "mean surge rising speed", and "mean surge falling time") and the "required attention degree" are recorded in association with each other for each patient (subject).

DESCRIPTION OF EMBODIMENT

An embodiment of the present invention will be described in detail below with reference to the drawings.

(Schematic Configuration of System)

Figure 1:
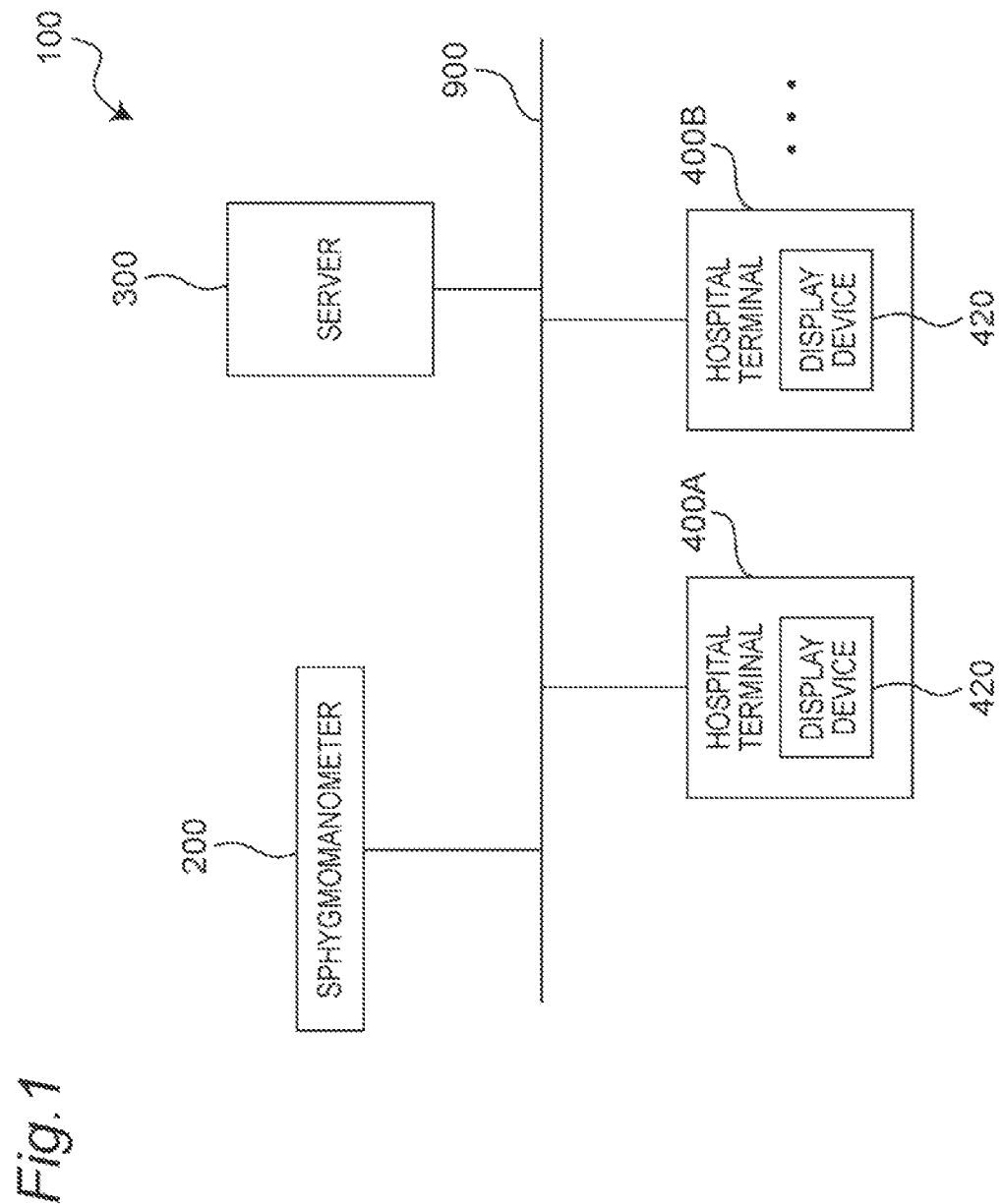
FIG. 1 is a block diagram illustrating an embodiment where a blood pressure-related information display device according to the present invention is configured as a system on a network.

FIG. 1 illustrates an example where a blood pressure-related information display device according to the present invention is configured as a system (denoted by a reference numeral 100) of an embodiment on a network. The system 100 includes a tonometry sphygmomanometer 200, a server 300 that detects and analyzes blood pressure surges from time-series data on blood pressure acquired by the sphygmomanometer 200, and hospital terminals 400A, 400B each having a display device 420 as a display screen. The sphygmomanometer 200, the server 300, and the hospital terminals 400A, 400B can communicate with each other over a network 900, which is an in-hospital local area network (LAN) in this example. Communication over the network 900 may be established by radio or wire. According to the present embodiment, the network 900 is an in-hospital local area network (LAN), but is not limited to the in-hospital LAN. The network 900 may be another type of network such as the Internet or may be one-to-one communication using a USB cable or the like. Although only two hospital terminals 400A, 400B (hereinafter, collectively denoted by a reference numeral 400) are illustrated in this example, three or more hospital terminals may be provided. Likewise, although only one sphygmomanometer 200 is illustrated in this example, two or more sphygmomanometers may be provided.

(Configuration of Sphygmomanometer)

Figure 2:
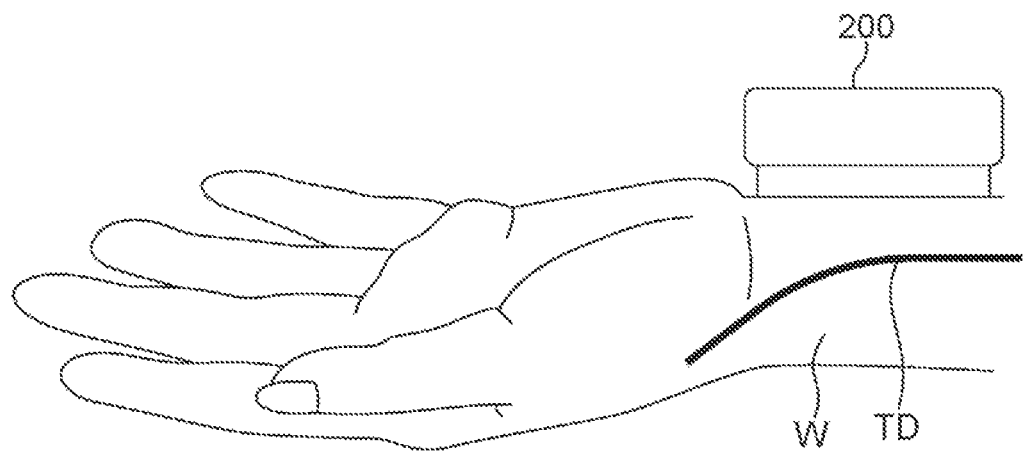
FIG. 2 is a perspective view illustrating an attached state where a sphygmomanometer included in the system is attached.
Figure 3:
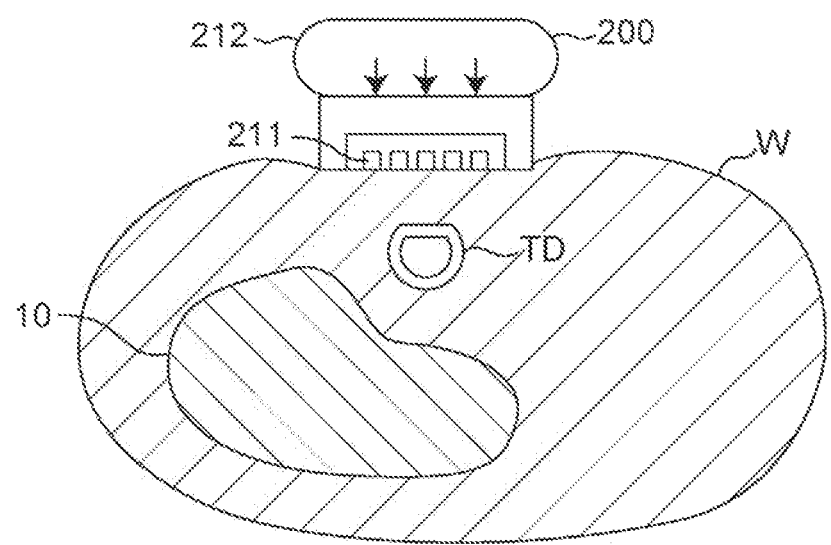
FIG. 3 is a cross-sectional view of the sphygmomanometer in the attached state.

The sphygmomanometer 200 illustrated in FIG. 1 is, for example, a tonometry sphygmomanometer as disclosed in JP 2018-42606 A. FIG. 2 illustrates an attached state where the sphygmomanometer 200 is attached to a wrist W of a subject. FIG. 3 illustrates a state where the sphygmomanometer 200 attached to the wrist W of the subject is in operation for blood pressure measurement. The sphygmomanometer 200 illustrated in FIGS. 2 and 3 continuously measures, for each pulse, a pressure pulse wave of a radial artery TD extending along a radius 10.

Figure 4:
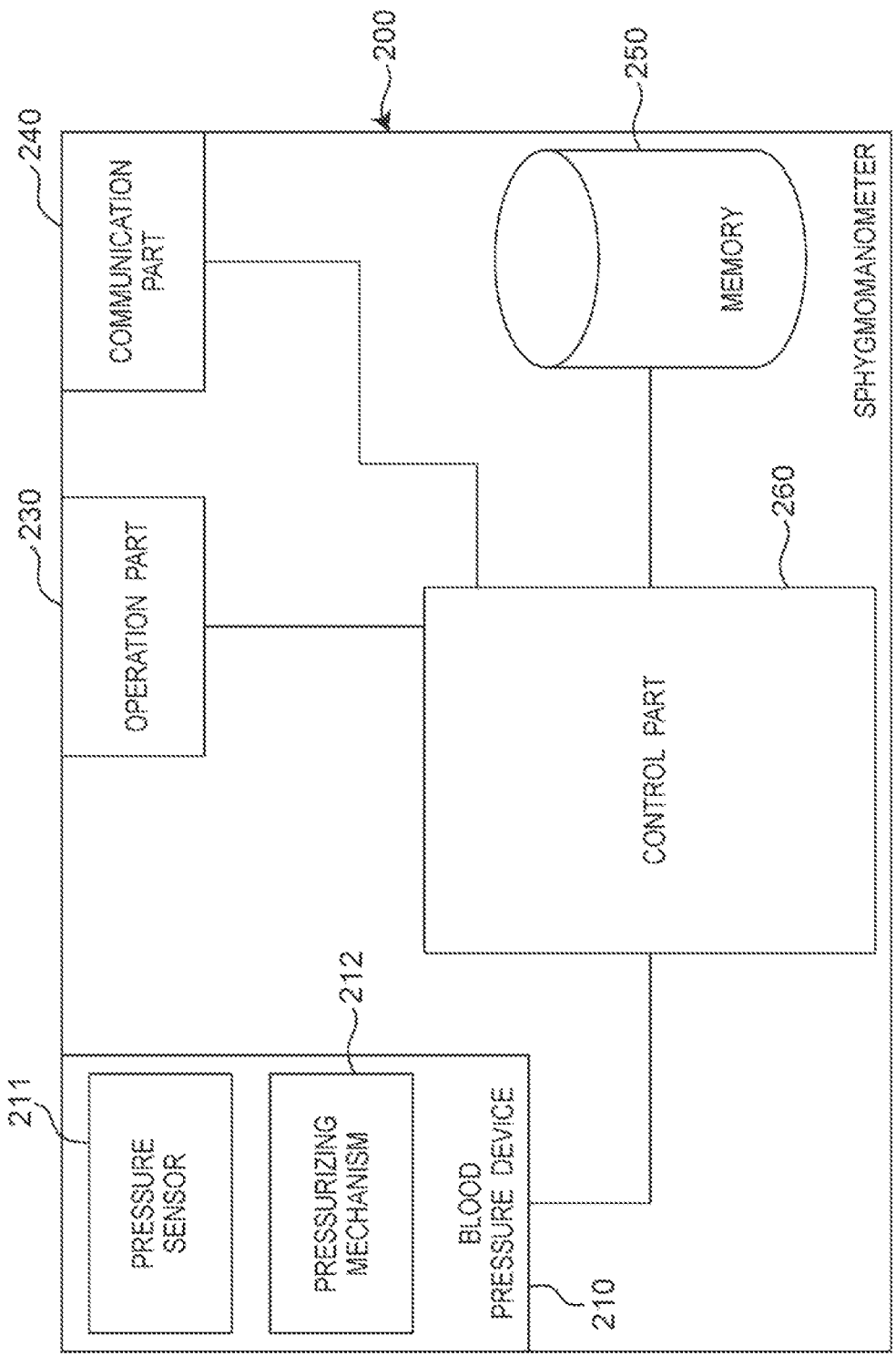
FIG. 4 is a diagram illustrating a block configuration of the sphygmomanometer.

FIG. 4 illustrates a block configuration of the sphygmomanometer 200. In this example, the sphygmomanometer 200 includes a blood pressure device 210, an operation part 230, a communication part 240, a memory 250, and a control part 260. Further, the blood pressure device 210 includes a pressure sensor 211 and a pressurizing mechanism 212.

Figure 7A:
FIG. 7A is a diagram illustrating time-series data on blood pressure of a subject for one night.

The pressurizing mechanism 212 applies a pressurizing force to a to-be-measured part as indicated by arrows in FIG. 3. When the pressurizing mechanism 212 applies the pressurizing force to the to-be-measured part, the pressure sensor 211 continuously detects a pressure pulse wave of the radial artery TD for each pulse by tonometry. Tonometry is a way under which, with a blood vessel pressed to be flat by the pressurizing mechanism 212, the pressure sensor 211 measures the pressure pulse wave to determine blood pressure. When the blood vessel is regarded as a circular tube having a uniform thickness, a relational expression between an internal pressure (blood pressure) of the blood vessel and an external pressure (pressure exerted by the pressure pulse wave) of the blood vessel can be derived in accordance with Laplace's law with consideration given to a wall of the blood vessel, regardless of the flow of blood in the blood vessel and the presence or absence of pulsation. Under the condition where the blood vessel is pressed to be flat on a pressed surface, this relational expression can make the pressure exerted by the pressure pulse wave and the blood pressure equal to each other by approximating the radii of the outer wall and inner wall of the blood vessel. This makes the pressure exerted by the pressure pulse wave equal to the blood pressure. Therefore, the sphygmomanometer 200 measures the blood pressure value of the to-be-measured part for each pulse. Then, the sphygmomanometer 200 generates blood pressure time-series data 801 in which a measurement time (time) is associated with blood pressure as illustrated in FIG. 7A, for example. The blood pressure time-series data 801 for one night contains pulse-synchronized peaks (peaks corresponding to SBP or DBP) for about 30,000 pulses.

The operation part 230 illustrated in FIG. 4 receives an instruction (input) from a user. The operation part 230 includes, for example, a plurality of buttons. The communication part 240 transmits and receives various data. The communication part 240 is connected to the network 900 illustrated in FIG. 1. The memory 250 illustrated in FIG. 4 stores various data. For example, the memory 250 can store a measurement value (blood pressure time-series data 801) measured by the blood pressure device 210, an SBP and DBP value for each pulse, a pulse rate, and the like. The memory 250 includes a random access memory (RAM), a read only memory (ROM), and the like. For example, various programs are stored in the memory 250 in an editable manner.

In this example, the control part 260 includes a central processing unit (CPU). For example, the control part 260 loads each program and each piece of data stored into the memory 250. Further, the control part 260 controls each component 210, 230, 240, 250 in accordance with the program thus loaded to bring the component into predetermined action (function). Further, the control part 260 performs, in the control part 260, predetermined computation, analysis, processing, and the like in accordance with the loaded program. Note that some or all of the functions to be run by the control part 260 may be implemented by hardware such as one or a plurality of integrated circuits.

The sphygmomanometer 200 outputs the blood pressure time-series data 801 in which a measurement time (time) is associated with blood pressure (see FIG. 7A), the SBP and DBP value for each pulse, the pulse rate, and the like to another device (in this example, the server 300) as measurement data.

(Configuration of Server)

Figure 5:
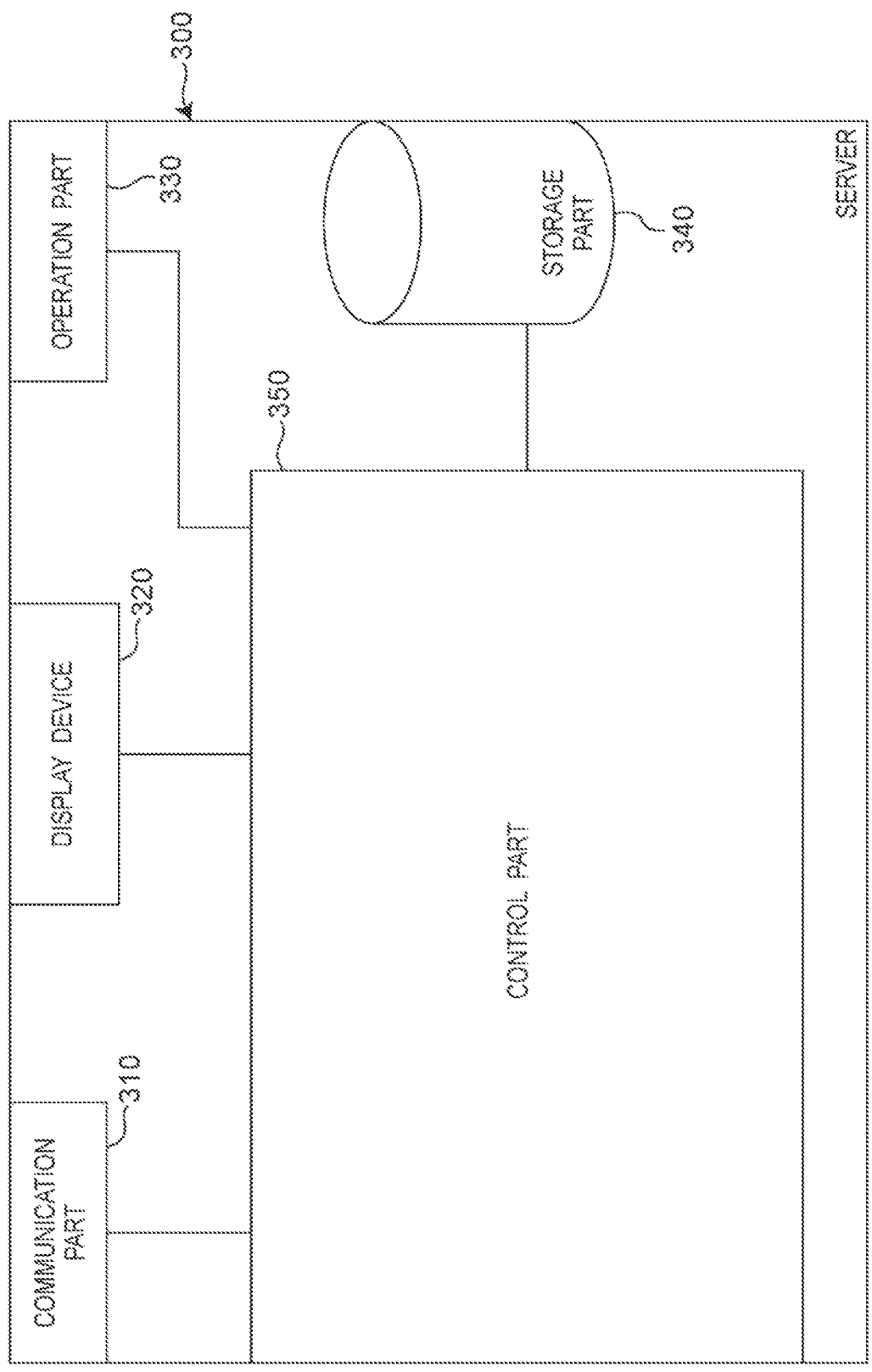
FIG. 5 is a diagram illustrating a block configuration of a server included in the system.

FIG. 5 illustrates a block configuration of the server 300. In this example, the server 300 includes a communication part 310, a display device 320, an operation part 330, a storage part 340, and a control part 350.

The communication part 310 transmits and receives various data. The communication part 310 is connected to the network 900 illustrated in FIG. 1. The communication part 310 receives, for example, the measurement data transmitted from the sphygmomanometer 200 over the network 900. Further, the communication part 310 transmits various output data generated by the control part 350 in the server 300 to the hospital terminal 400 over the network 900.

The display device 320 illustrated in FIG. 5 has a display screen for displaying various images. The display device 320 can display, in a visually recognizable form, results of various analyses and the like made by the control part 350. The display device 320 can further display, in a visually recognizable form, predetermined information in response to a request from the user via the operation part 330. For example, the display device 320 may display, in a visually recognizable form, information (data) stored in the storage part 340. For example, a liquid crystal display, an organic electro luminescence (EL) display, or the like may be used as the display device 320.

The operation part 330 receives a predetermined operation (instruction) from the user. For example, the operation part 330 includes a mouse, a keyboard, and the like. When a touchscreen monitor is used as the display device 320, the display device 320 has not only a display function but also a function as the operation part 330.

The storage part 340 stores various data. For example, the storage part 340 can store the measurement data such as the measurement value (blood pressure time-series data 801), the SBP and DBP value for each pulse, the pulse rate, and the like measured by the blood pressure device 210. The storage part 340 can further store various output data generated by the control part 350. The storage part 340 includes a RAM, a ROM, and the like. The storage part 340 also stores various programs in an editable manner. In this example, the storage part 340 stores a program for implementing a blood pressure-related information display method (to be described later). Note that a magnetic disk (hard disk (HD), flexible disk (FD)), an optical disc (compact disc (CD), digital versatile disc (DVD), Blu-ray disc (BD)), a magneto-optical disk (MO), a semiconductor memory (memory card, SSD), or the like may be used as a storage medium of a secondary storage device serving as an auxiliary for a storage area of the storage part 340.

In this example, the control part 350 includes a CPU. For example, the control part 350 loads each program and each piece of data stored into the storage part 340. Further, the control part 350 controls each component 310, 320, 330, 340 in accordance with the program thus loaded to bring the component into predetermined action (function). Further, the control part 350 performs, in the control part 350, predetermined computation, analysis, processing, and the like in accordance with the loaded program. Note that some or all of the functions to be run by the control part 350 may be implemented by hardware such as one or a plurality of integrated circuits. How the control part 350 operates will be described in detail later.

(Configuration of Hospital Terminal)

The hospital terminal 400 illustrated in FIG. 1 is a general personal computer in this example. The hospital terminal 400 may be a mobile terminal such as a tablet instead of such a personal computer.

The display device 420 included in the hospital terminal 400 has a display screen for displaying various images. For example, the display device 420 displays, in a visually recognizable form, images corresponding to various output data received from the server 300. The display device 420 can further display, in a visually recognizable form, predetermined information in response to user operation. For example, a liquid crystal display, an organic EL display, or the like may be used as the display device 420.

(Operation of System)

Figure 6:
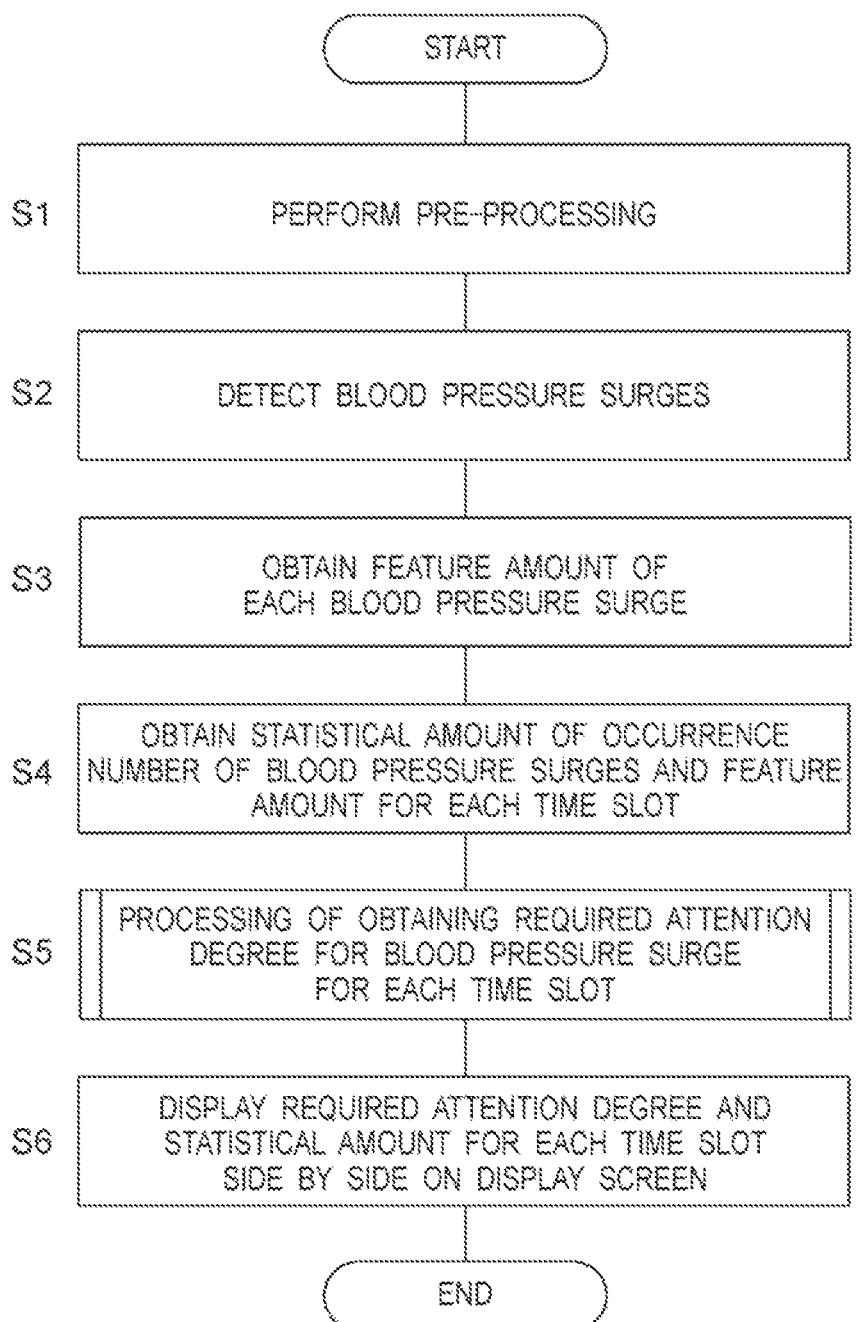
FIG. 6 is a diagram schematically illustrating an operation flow of first processing of displaying blood pressure-related information performed by the system.

The system 100 is capable of executing the following first blood pressure-related information display method, the first blood pressure-related information display method primarily including processing of detecting and analyzing the blood pressure surges in the server 300 illustrated in steps S1 to S5 in FIG. 6 and processing of displaying blood pressure surge-related information in the hospital terminal 400 illustrated in step S6 in FIG. 6. Note that the system 100 is further capable of executing a second blood pressure-related information display method (to be described later).

[First Blood Pressure-Related Information Display Method]

Under the first blood pressure-related information display method, information on the blood pressure surge of the subject is displayed in a visualized form for each time slot.

It is assumed that measurement data containing the blood pressure time-series data 801 for one night (see FIG. 7A), the SBP and DBP value for each pulse, the pulse rate, and the like of a certain subject is already measured by the sphygmomanometer 200 and stored in the storage part 340 of the server 300 over the network 900. Note that the sphygmomanometer 200 may first transmit the measurement data to any one of the hospital terminals 400, and the relevant hospital terminal 400 may transmit the measurement data to the server 300.

(1) Pre-Processing (Step S1 in FIG. 6)

In step S1 in FIG. 6, the control part 350 of the server 300 acts as a pre-processing part to perform pre-processing such as smoothing the blood pressure time-series data and removing noise from the blood pressure time-series data using a well-known moving average or the like, or removing high frequency components from the blood pressure time-series data using a low-pass filter.

Furthermore, the control part 350 of the server 300 extracts, from the blood pressure time-series data 801, a valid section to be subjected to blood pressure surge detection and analysis. That is, of the blood pressure time-series data 801, a section affected by disturbance (noise or the like) is removed as an invalid section, and a section not affected by the disturbance is left as the valid section. This allows a reduction in risk of erroneously detecting a variation due to noise as a blood pressure surge. This further allows a reduction in processing time for the blood pressure surge detection and analysis.

The following processing (steps S2 to S6 in FIG. 6) is performed on this valid section.

(2) Processing of Detecting Blood Pressure Surge (Step S2 in FIG. 6)

Figure 7B:
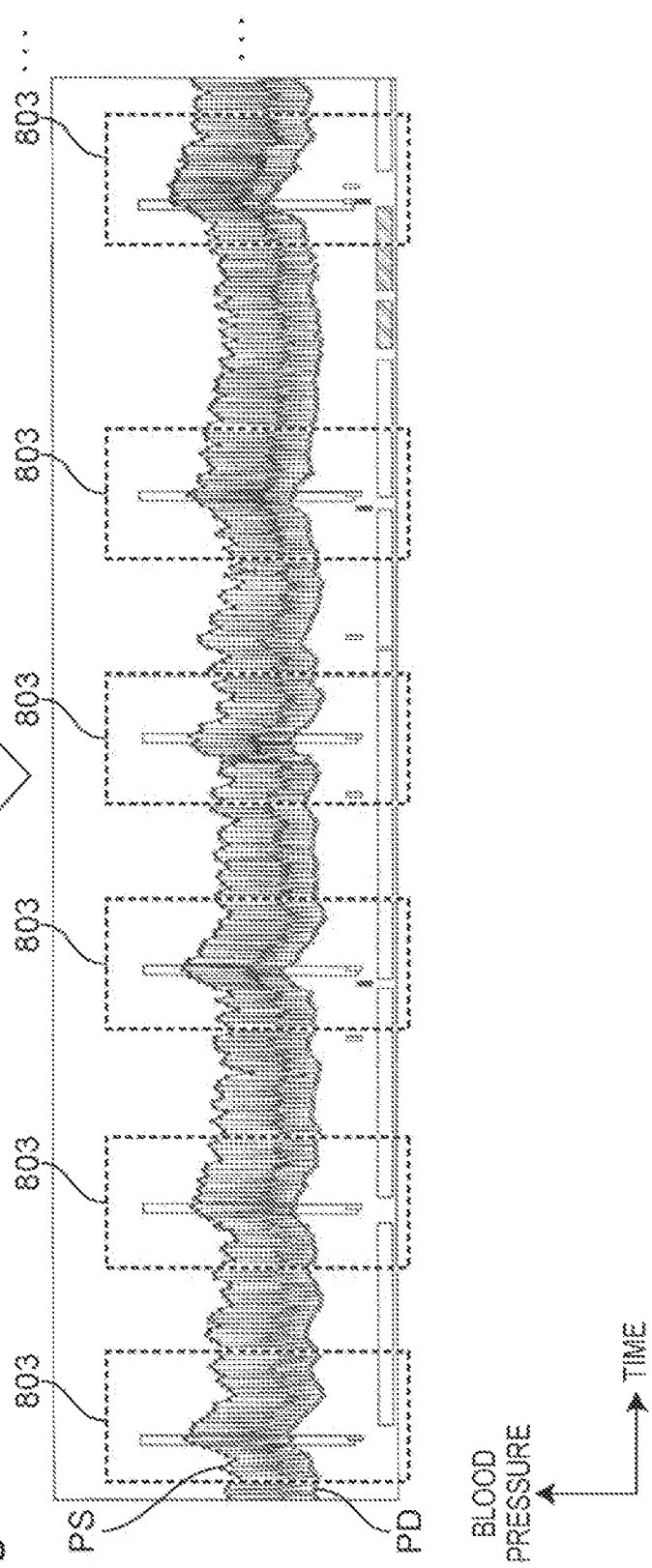
FIG. 7B is an enlarged view of a part of FIG. 7A, illustrating blood pressure surges detected on the time-series data.

Next, in step S2 in FIG. 6, the control part 350 of the server 300 acts as a blood pressure surge detection part to detect a blood pressure surge from (the valid section of) the blood pressure time-series data 801 on the subject based on predetermined determination criteria as disclosed in, for example, Japanese patent application No. 2017-048946 and Japanese Patent Application No. 2017-050066. As a result, for example, a plurality of blood pressure surges are detected as indicated by dashed-line rectangular frames 803, 803, . . . in FIG. 7B. It is said that several hundred blood pressure surges may occur for one night. In this example, systolic blood pressure (SBP) for each pulse is plotted (in FIG. 7B, as an example, a portion of the SBP is denoted by PS) and connected by an envelope. Likewise, diastolic blood pressure (DBP) for each pulse is plotted (in FIG. 7B, as an example, a portion of the DBP is denoted by PD) and connected by an envelope.

The "predetermined determination criteria" for detection of a blood pressure surge refer to, as illustrated in FIG. 8 (an example of the waveform of the blood pressure surge is represented by a curve C), for example, that a range from a surge start point P1 to a surge peak point P2 falls within a peak detection section (for example, a period of 15 pulses), that a difference (surge variation amount) L1 between a systolic blood pressure value (SBP) at the surge start point P1 and a systolic blood pressure value (SBP) at the peak point P2 is equal to or greater than 20 mmHg (or 15 mmHg), that a period T1 between the surge start point P1 and the peak point P2 is longer than a period of five pulses, and that a period T3 between the peak point P2 and a surge end point P4 is longer than a period of seven pulses. In this example, the surge start point P1 is defined as a point before the peak point P2 where the systolic blood pressure value (SBP) becomes the lowest. The surge end point P4 is defined as a point after the peak point P2 where the blood pressure falls by L1×0.75 (=L3) from the peak point P2.

(3) Processing of Obtaining Feature Amount (Step S3 in FIG. 6)

Next, in step S3 in FIG. 6, the control part 350 of the server 300 acts as a feature amount calculation part to obtain, for each blood pressure surge (for example, surge No. 1, 2, . . . ) detected for the subject, a "surge variation amount", a "surge peak value", a "surge time", a "surge rising speed", and a "surge falling time" as the feature amount indicating characteristics of the blood pressure surge in this example. The "surge variation amount" refers to the difference L1 between the systolic blood pressure value (SBP) at the surge start point P1 and the systolic blood pressure value (SBP) at the peak point P2 illustrated in FIG. 8. The "surge peak value" refers to the systolic blood pressure value (SBP) at the peak point P2. The "surge time" refers to a length of a period (=T1+T2) between the surge start point P1 and the surge end point P4. The "surge rising speed" refers to a rising speed (=L1/T1) of the systolic blood pressure value (SBP) from the surge start point P1 to the peak point P2. The "surge falling time" refers to a period T3 between the peak point P2 and the surge end point P4. In a surge unit table (not illustrated) provided in the storage part 340, for each detected blood pressure surge (surge No. 1, 2, . . . ), the "surge variation amount", the "surge peak value", the "surge time", the "surge rising speed", and the "surge falling time" are recorded in association with each other as the feature amount of each blood pressure surge.

(4) Processing of Obtaining Statistical Amount (Step S4 in FIG. 6)

Next, in step S4 in FIG. 6, the control part 350 of the server 300 acts as a statistical amount calculation part to perform statistical processing on the occurrence number of the blood pressure surges detected for the subject and the feature amount obtained in step S3 to obtain statistical amounts for each of time slots in this example. In this example, the statistical processing is processing of counting the occurrence number of the blood pressure surges for each of the time slots and averaging the feature amount of the blood pressure surges for each of the time slots.

In this example, as shown in the time slot table in FIG. 10, the statistical amounts include a "surge occurrence number" that is the occurrence number of blood pressure surges, and a "mean surge variation amount" and a "mean surge peak value" serving as the feature amount of the blood pressure surges. In the time slot table in FIG. 10, the "surge occurrence number", the "mean surge variation amount", the "mean surge peak value", a "mean surge time", and a "mean surge rising speed" are recorded in association with each other for each of the time slots of "10 PM RANGE", "11 PM RANGE", "0 AM RANGE", . . . , and "7 AM RANGE" shown in a "time slot" column (for the sake of simplicity, the "mean surge time" and the "mean surge rising speed" are not shown). In this example, the "surge occurrence number" is recorded as "3", "11", "14", . . . , and "1" [times], the "mean surge variation amount" is recorded as "22", "25", "27", . . . , and "21" [mmHg], and the "mean surge peak value" is recorded as "141", "143", "149", . . . , and "149" [mmHg] for each of the time slots of "10 PM RANGE", "11 PM RANGE", "0 AM RANGE", . . . , and "7 AM RANGE". An "occurrence number index" column, a "variation amount index" column, a "peak value index" column, and a "required attention degree" column shown in the time slot table in FIG. 10 will be described later.

Note that the statistical processing may include, in addition to the averaging processing described above, processing of obtaining a standard deviation, processing of obtaining a maximum value and a minimum value, processing of obtaining quartiles, processing of creating a bar graph, processing of creating a scatter plot, and the like.

Objects on which the statistical processing is performed may include: in addition to those described above, i) Systolic blood pressure (SBP) value and diastolic blood pressure (DBP) value for each pulse, ii) Pulse rate (PR) (pulse/minute), iii) Combination of the above-described feature amounts of the blood pressure surges using four arithmetic operations, and the like. Note that, as the blood pressure surge occurs, the pulse rate gradually increases to a peak value, and then shows a descending change (mountain-shaped waveform), like the blood pressure surge.

The statistical processing is performed every time slot as a unit period, in this example, every hour, but may be performed at any timing. For example, the statistical processing is performed every 30 minutes, every two hours, every three hours, or the like.

(5) Processing of Obtaining Required Attention Degree (Step S5 in FIG. 6)

Next, in step S5 in FIG. 6, the control part 350 of the server 300 acts as a required attention degree calculation part to obtain, for each time slot, a required attention degree (denoted by DC) indicating a level of attention being required to the blood pressure surge for the subject.

In this example, the control part 350 obtains the required attention degree DC for each time slot shown in the time slot table in FIG. 10 based on a result of comparison between the "surge occurrence number", the "mean surge variation amount", and the "mean surge peak value", and respective predetermined thresholds.

In this example, two thresholds (denoted by $\alpha 1$, $\alpha 2$ and satisfy $\alpha 1 < \alpha 2$) different in magnitudes are defined as thresholds for the "surge occurrence number". In this example, it is assumed that $\alpha 1$ and $\alpha 2$ default to 10 times and 30 times, respectively.

In this example, two threshold values (denoted by $\beta 1$, $\beta 2$ and satisfy $\beta 1 < \beta 2$) different in magnitude are defined as thresholds for the "mean surge variation amount". In this example, it is assumed that $\alpha 1$ and $\alpha 2$ default to 25 mmHg and 30 mmHg, respectively.

In this example, two threshold values (denoted by $\gamma 1$, $\gamma 2$ and satisfy $\gamma 1 < \gamma 2$.) different in magnitude are defined as thresholds for the "mean surge peak value". In this example, it is assumed that $\gamma 1$, $\gamma 2$ default to 120 mmHg and 150 mmHg, respectively.

Figure 11:
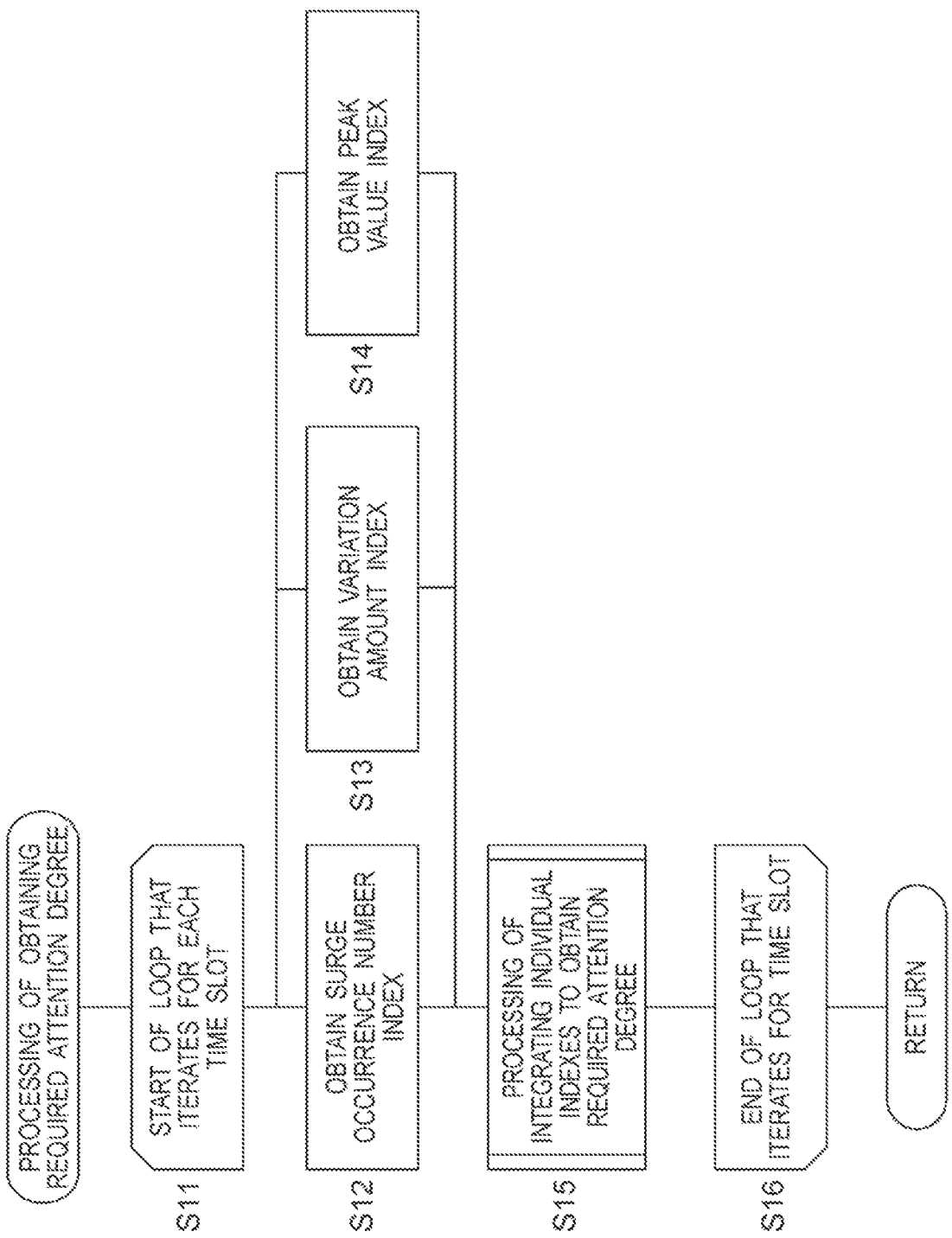
FIG. 11 is a diagram illustrating a detailed flow of processing of obtaining a required attention degree indicating a level of attention being required to the blood pressure surge.

Specifically, in order to obtain the required attention degree DC, the control part 350 executes the flow of the processing of obtaining the required attention degree shown in FIG. 11.

First, as shown in step S11 in FIG. 11, the control part 350 starts a loop that iterates for each time slot. From the time slot table in FIG. 10, the control part 350 retrieves the surge occurrence number, the mean surge variation amount, and the mean surge peak value for a certain time slot (referred to as a "time slot of interest", and, for the first iteration of the loop, the time slot of interest is "10 PM RANGE"). Next, the control part 350 acts as an individual index calculation part (included in the required attention degree calculation part) to obtain an individual index indicating a level of attention being required to the "surge occurrence number" (referred to as an "occurrence number index" and denoted by ID1) based on a result of comparison with the thresholds α1, α2 as shown in step S12. Similarly, the control part 350 obtains, as shown in step S13, an individual index indicating a level of attention being required to the "mean surge variation amount" (referred to as a "variation amount index" and denoted by ID2) based on a result of comparison with the thresholds β1, β2. The control part 350 further obtains, as shown in step S14, an individual index indicating a level of attention being required to the "mean surge peak value" (referred to as a "peak value index" and denoted by ID3) based on a result of comparison with the thresholds γ1, γ2. Note that steps S12 to S14 may be executed in different orders or may be executed in parallel with each other.

Since the thresholds for the three individual indexes are sets of two thresholds α1 and α2, β1 and β2, and γ1 and γ2, each having different magnitudes, the "occurrence number index" ID1, the "variation amount index" ID2, and the "peak value index" ID3 are each obtained as one of three levels of low, medium, and high as shown in the criteria table in FIG. 9. Specifically, the "occurrence number index" ID1 is obtained as one of the three levels, "low" when the occurrence number is equal to or less than 10 times, "medium" when the occurrence number is greater than 10 times and equal to or less than 30 times, and "high" when the occurrence number is greater than 30 times, based on the thresholds α1, α2 (as described above, α1=10 times, and α2=30 times). The "variation amount index" ID2 is obtained as one of the three levels, "low" when the variation amount is equal to or less than 25 mmHg, "medium" when the variation amount is greater than 25 mmHg and equal to or less than 30 mmHg, and "high" when the variation amount is greater than 30 mmHg, based on the thresholds β1, β2 (as described above, β1=25 mmHg and β2=30 mmHg). Further, the "peak value index" ID3 is obtained as one of the three levels, "low" when the peak value is equal to or less than 120 mmHg, "medium" when the peak value is greater than 120 mmHg and equal to or less than 150 mmHg, and "high" when the peak value is greater than 150 mmHg, based on the thresholds γ1, γ2 (as described above, γ1=120 mmHg and γ2=150 mmHg).

For example, for the time slot of interest "10 PM RANGE" for the first iteration, the "occurrence number index" ID1 is obtained as "low" since the "surge occurrence number" is three times, the "variation amount index" ID2 is obtained as "low" since the "mean surge variation amount" is 22 mmHg, and the "peak value index" ID3 is obtained as "medium" since the "mean surge peak value" is 141 mmHg. The "occurrence number index" ID1, the "variation amount index" ID2, and the "peak value index" ID3 thus obtained are each recorded in association with the time slot of interest ("10 PM RANGE" for the first iteration) in the time slot table in FIG. 10.

Next, as shown in step S15 in FIG. 11, the control part 350 acts as an integration processing part (included in the required attention degree calculation part) to integrate the individual indexes to obtain, as one of the three levels, the required attention degree DC indicating a level of attention being required to the blood pressure surge for the time slot of interest.

In this example, in a way for integrating the individual indexes, one (level) of the highest frequency among the three levels of "low", "medium", and "high", indicated by the individual indexes is determined as the required attention degree DC (majority rule). According to the majority rule, the required attention degree DC is determined from the viewpoint of providing a representative one (level) among the individual indexes.

For example, for "10 PM RANGE" that is the time slot of interest for the first iteration, since the "occurrence number index" ID1 is "low", the "variation amount index" ID2 is "low", and the "peak value index" ID3 is "medium", "low" that is of the highest frequency among the levels is taken as the required attention degree DC. The required attention degree DC thus obtained is recorded in the "required attention degree" field in association with the time slot of interest ("10 PM RANGE") in the time slot table in FIG. 10.

For the iteration next to the first iteration described above, the time slot of interest is "11 PM RANGE". For the time slot of interest "11 PM RANGE", the "occurrence number index" ID1 is obtained as "medium" since the "surge occurrence number" is 11 times, the "variation amount index" ID2 is obtained as "low" since the "mean surge variation amount" is 25 mmHg, and the "peak value index" ID3 is obtained as "medium" since the "mean surge peak value" is 143 mmHg (steps S12 to S14 in FIG. 11). As a result, the required attention degree DC is obtained as "medium". The required attention degree DC thus obtained is recorded in the "required attention degree" field in association with the time slot of interest ("11 PM RANGE") in the time slot table in FIG. 10 (step S15 in FIG. 11).

As described above, the "occurrence number index" ID1, the "variation amount index" ID2, the "peak value index" ID3, and the "required attention degree" DC are sequentially obtained for each time slot of interest and are sequentially recorded in the time slot table in FIG. 10. In the example shown in the time slot table in FIG. 10, "low", "medium", "medium", . . . , and "low" for the "occurrence number index" ID1, "low", "medium", "medium", . . . , and "low" for the "variation amount index" ID2, "medium", "medium", "medium", . . . , and "medium" for the "peak value index" ID3, and "low", "medium", "medium", . . . , and "low" for the "required attention degree" DC are recorded in association with each of the time slots, i.e. "10 PM RANGE", "11 RANGE", "0 AM RANGE", . . . , and "7 AM RANGE".

When the "occurrence number index" ID1, the "variation amount index" ID2, the "peak value index" ID3, and the "required attention degree" DC have been recorded for all the time slots, the loop that iterates for each time slot comes to an end as shown in step S16 in FIG. 11.

As described above, the system 100 allows the required attention degree DC to be obtained by simple arithmetic processing.

Note that, in the above-described example, the thresholds α1, α2 for the "surge occurrence number", the thresholds β1, β2 for the "mean surge variation amount", and the thresholds γ1, γ2 for the "mean surge peak value" are each set to a corresponding default value, but are not limited to such default values. For example, the user (typically, a system administrator) may set the thresholds α1, α2, β1, β2, γ1, γ2 in a variable manner by using the operation part 330 of the server 300 as an input part before the processing of obtaining the required attention degree (step S5 in FIG. 6). This allows the experience of the user (typically, a doctor) to be reflected in the threshold (standard) for use in obtaining each individual index (the "occurrence number index" ID1, the "variation amount index" ID2, and the "peak value index" ID3) as one of the three levels, and accordingly, in the standard for use in obtaining the required attention degree DC as one of the three levels.

In the above-described example, the majority rule is used as a way for integrating the individual indexes (the "occurrence number index" ID1, the "variation amount index" ID2, and the "peak value index" ID3), but the way is not limited to the majority rule. As a way for integrating the individual indexes, the highest one (level) among the three levels of "low", "medium", and "high", indicated by the individual indexes may be determined as the required attention degree DC (higher-level priority rule). In this case, for example, for "10 PM RANGE" in the time slot table in FIG. 10, since the "occurrence number index" ID is "low", the "variation amount index" ID2 is "low", and the "peak value index" ID3 is "medium", the highest "medium" level among the levels is taken as the required attention degree DC. According to the higher-level priority rule, the required attention degree DC is determined from the viewpoint that any individual index requiring even little higher attention should be pointed out.

Further, in the above-described example, the three individual indexes including the "occurrence number index" ID1, the "variation amount index" ID2 and the "peak value index" ID3 are used as the individual indexes, but the individual indexes are not limited to such three ones. As the individual indexes, in addition to the above-described three individual indexes, an individual index indicating a level of attention being required to the "mean surge time" (referred to as a "surge time index"), an individual index indicating a level of attention being required to the "mean surge rising speed" (referred to as a "surge rising speed index"), and an individual index indicating a level of attention being required to the "surge falling time" (referred to as a "surge falling time index") may be used. Further, in addition to such individual indexes, individual indexes indicating a level of attention being required to statistical amounts such as a standard deviation, a maximum value and minimum value, and quartiles other than the mean values may be used. Further, individual indexes indicating a level of attention being required to the following various kinds of statistical amounts:

i) Systolic blood pressure (SBP) value and diastolic blood pressure (DBP) value for each pulse, ii) Pulse rate (PR) (pulse/minute), and iii) Combination of the above-described feature amounts of the blood pressure surge using four arithmetic operations, may be used.

(6) Processing of Displaying Blood Pressure Surge-Related Information (Step S6 in FIG. 6)

Figure 12:
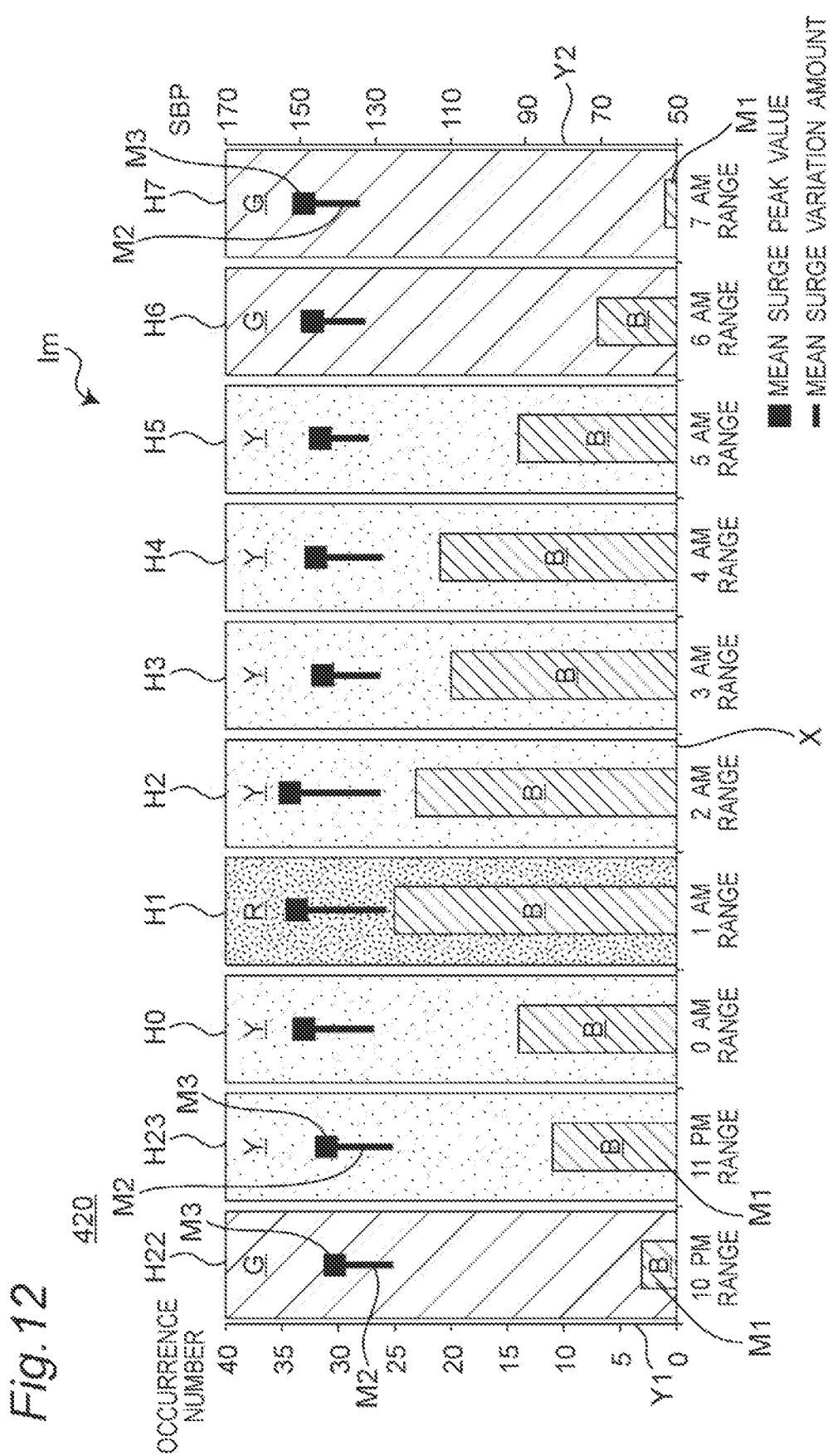
FIG. 12 is a diagram illustrating a display example where the required attention degree obtained and the statistical amounts are displayed side by side for each time slot on a display screen.

Next, in step S6 in FIG. 6, in this example, the control part 350 of the server 300 creates image data (denoted by Im) where the required attention degree DC, the "surge occurrence number", "mean surge variation amount", and "mean surge peak value" obtained for the subject are displayed side by side for each time slot. Any of the hospital terminals 400 (400A, 400B, . . . ) receives the image data Im from the server 300 over the network 900. The hospital terminal 400 acts as a display processing part to display, in graph form, the image data Im on the display screen of the display device 420 as illustrated in FIG. 12.

In this example, the image data Im includes rectangular closed areas H22, H23, H0, . . . , and H7 that correspond to the respective time slots "10 PM RANGE", "11 PM RANGE", "0 AM RANGE", . . . , and "7 AM RANGE" and are set, on the display screen, side by side along the progress of the time slots (along a horizontal axis X). Each of the closed area H22, H23, H0, . . . , and H7 is given a specific color according to the required attention degree DC in a corresponding time slot. As the "specific color", in this example, three colors, green (G) corresponding to "low" of the required attention degree DC, yellow (Y) corresponding to "medium" of the required attention degree DC, and red (R) corresponding to "high" of the required attention degree DC, are used.

For example, in the time slot table in FIG. 10, the "required attention degree" DC is recorded as "low" for the time slot "10 PM RANGE". Accordingly, in the image data 1m in FIG. 12, green (G) is applied to the closed area H22. Further, in the time slot table in FIG. 10, the "required attention degree" DC is recorded as "medium" for the time slot "11 PM RANGE". Accordingly, in the image data Im in FIG. 12, yellow (Y) is applied to the closed area 1123. Further, in the time slot table in FIG. 10, the "required attention degree" DC is recorded as "high" for the time slot "1 AM RANGE". Accordingly, in the image data Im in FIG. 12, red (R) is applied to the closed area H1. As described above, in the image data Im, the specific color according to the required attention degree DC in a corresponding time slot is applied to each of the closed areas H22, H23, H0, . . . , and H7.

This allows the user to intuitively grasp changes in the required attention degree DC (that is, the level of attention being required to the blood pressure surge) among the time slots by viewing the display screen of the display device 420.

Furthermore, in this example, on the display screen of the display device 420, the image data Im is displayed such that graphs showing the "surge occurrence number", the "mean surge variation amount", and the "mean surge peak value" are superimposed on each of the plurality of closed areas H22, 1123, H0, . . . , and H7.

In this example, the "surge occurrence number" is represented as a bar graph M1 for each time slot. Blue (B) is applied to each bar forming the bar graph M1. Blue (B) is different from any specific color (green (G), yellow (Y), red (R)) for use in indicating the required attention degree DC, and thus can be easily distinguished from a background color (color of each of the closed areas H22, 1123, H0, . . . , and H7). The user can intuitively grasp changes in the "surge occurrence number" among the time slots by viewing the bar graph M1. Note that, in this example, a scale for the "surge occurrence number" is provided on the left side along a vertical axis Y1.

Further, in this example, the "mean surge peak value" is represented as a square dot-shaped mark M3 for each time slot. The dot-shaped mark M3 may be a circle, a triangle, or the like, instead of a square. The "mean surge variation amount" is represented as a line-shaped mark M2 extending downward from each dot-shaped mark M3 representing the "mean surge peak value". A color of the dot-shaped mark M3 and the line-shaped mark M2 may be any color as long as the color can be easily distinguished from the background color (color of each of the closed areas H22, H23, H0, . . . , and H7), and may be, for example, black (Bk). The user can intuitively grasp changes in the "mean surge variation amount" and the "mean surge peak value" among the time slots by viewing the marks M2, M3. In this example, a scale for the "mean surge variation amount" and the "mean surge peak value" is provided on the right side along the vertical axis Y2.

Further, the user can intuitively grasp a reason or basis that the required attention degree DC (color of each of the closed areas H22, H23, H0, . . . , and H7) is green (G) (low level), yellow (Y) (medium level), or red (R) (high level) for each time slot by viewing the graphs (the bar graph M1 and the marks M2, M3) representing the "surge occurrence number", the "mean surge variation amount", and the "mean surge peak value".

As described above, under the blood pressure-related information display method, the information on the blood pressure surge is displayed in a visualized form for each time slot. As a result, the user can grasp changes in the required attention degree DC indicating the level of attention being required to the blood pressure surge and the statistical amounts of the feature amount indicating the characteristics of the blood pressure surge among the time slots by viewing the display screen of the display device 420. This allows, for example, a doctor to grasp a tendency of the condition of the patient (subject) for each of the time slots and easily give advice to the patient at the time of consultation. Further, when there is a request for detailed analysis of the waveform of the blood pressure surge, a doctor can first analyze a surge case in a time slot in which the required attention degree DC is high and thus can make an efficient analysis. Furthermore, the information (including the image data Im) displayed on the display screen of the display device 420 helps to study the relevancy between the blood pressure surge and a cardiovascular event (angina pectoris, myocardial infarction, ischemic heart disease, or the like) in addition to the diagnosis and treatment of SAS, and may lead to new clinical findings.

Note that, in the above-described example, both the required attention degree DC indicating the level of attention being required to the blood pressure surge and the graph (the bar graph M1 and the marks M2, M3) of the statistical amounts of the feature amount indicating the characteristics of the blood pressure surge are displayed side by side for each time slot on the display screen of the display device 420, but the present invention is not limited to such a configuration. Only one of the required attention degree DC indicating the level of attention being required to the blood pressure surge or the graph of the statistical amounts of the feature amount indicating the characteristics of the blood pressure surge may be displayed side by side for each time slot.

[Second Blood Pressure-Related Information Display Method]

Figure 13:
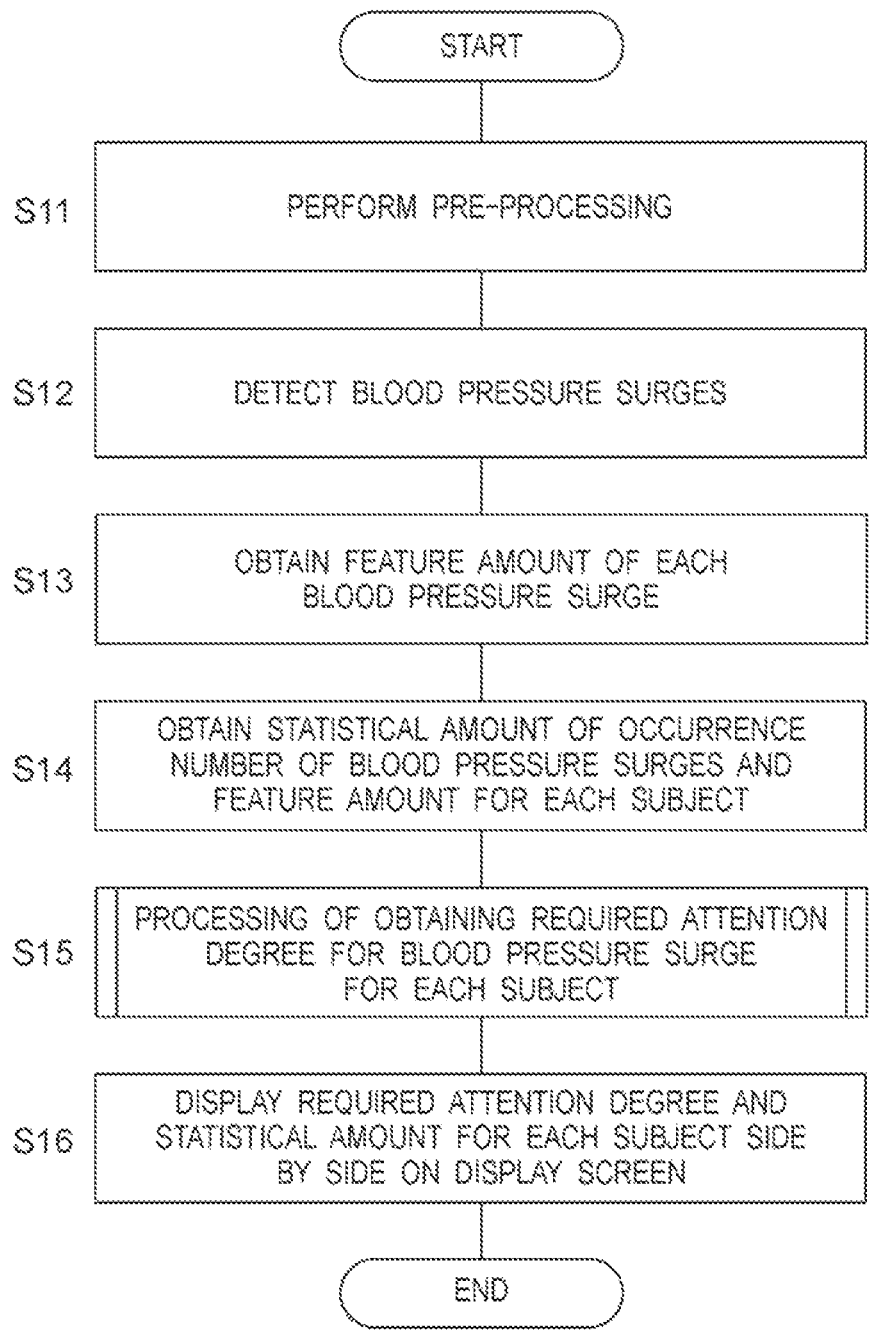
FIG. 13 is a diagram schematically illustrating an operation flow of second processing of displaying blood pressure-related information performed by the system.

The system 100 executes the following second blood pressure-related information display method, the second blood pressure-related information display method primarily including processing of detecting and analyzing blood pressure surges in the server 300 shown in steps S11 to S15 in FIG. 13 and processing of displaying blood pressure surge-related information in the hospital terminal 400 shown in step S16 in FIG. 13.

It is considered clinically important to display, in a visualized form, blood pressure-related information such as occurrence number of blood pressure surges, a surge peak value, a surge variation amount, and a risk evaluated based on the information on the blood pressure surge on a subject-by-subject basis. However, as far as the present applicants know, a technique for displaying, in a visualized form, information on the blood pressure surge for each subject has not been known. Therefore, under the second blood pressure-related information display method, information on the blood pressure surge for a plurality of subjects are displayed in a visualized form on a subject-by-subject basis.

It is assumed that measurement data including the blood pressure time-series data 801 for one night (see FIG. 7A), the SBP value and DBP value for each pulse, the pulse rate, and the like of each of the plurality of subjects is already measured by the sphygmomanometer 200 and stored, on a subject-by-subject basis, in the storage part 340 of the server 300 over the network 900. Note that the measurement data on the plurality of subjects may be measured by a sphygmomanometer 200 assigned to each subject among a plurality of the sphygmomanometers 200 connected to the network 900. Further, each sphygmomanometer 200 may first transmit the measurement data to any one of the hospital terminals 400, and the relevant hospital terminal 400 may transmit the measurement data to the server 300.

(1) From pre-processing to processing of obtaining feature amount (Steps S 11 to S13 in FIG. 13)

Under the second blood pressure-related information display method, steps S11 to S13 in FIG. 13 are executed for each subject in the same manner as steps S1 to S3 in FIG. 6.

That is, in step S11 in FIG. 13, the control part 350 of the server 300 acts as a pre-processing part to perform, on a subject-by-subject basis, pre-processing such as smoothing the blood pressure time-series data and removing noise from the blood pressure time-series data using a well-known moving average or the like, and removing high frequency components from the blood pressure time-series data using a low-pass filter. Furthermore, the control part 350 of the server 300 extracts, from the blood pressure time-series data 801, a valid section to be subjected to blood pressure surge detection and analysis. The following processing (steps S12 to S16 in FIG. 13) is executed for this valid section.

Next, in step S12 in FIG. 13, the control part 350 of the server 300 acts as a blood pressure surge detection part to detect blood pressure surges, on a subject-by-subject basis, from (the valid section of) the blood pressure time-series data 801 based on predetermined determination criteria.

Next, in step S13 in FIG. 13, the control part 350 of the server 300 acts as a feature amount calculation part to calculate, for each blood pressure surge (for example, surge No. 1, 2, . . . ) thus detected, a "surge variation amount", a "surge peak value", a "surge time", a "surge rising speed", and a "surge falling time" as the feature amount indicating characteristics of the blood pressure surge on a subject-by-subject basis in this example. In a surge unit table (not illustrated) provided in the storage part 340, for each detected blood pressure surge (surge No. 1, 2, . . . ), the "surge variation amount", the "surge peak value", the "surge time", the "surge rising speed", and the "surge falling time" are recorded in association with each other as the feature amount of the blood pressure surges on a subject-by-subject basis.

(2) Processing of Obtaining Statistical Amount (Step S14 in FIG. 13)

Next, in step S14 in FIG. 13, the control part 350 of the server 300 acts as a statistical amount calculation part to perform statistical processing on the occurrence number of the blood pressure surges detected and the feature amount calculated in step S13 for each subject to calculate statistical amounts in this example. In this example, the statistical processing is processing of counting the occurrence number of blood pressure surges for one night (from 10 PM RANGE to 7 AM RANGE) and averaging the feature amount of the blood pressure surges for one night.

In this example, as shown in a patient-by-patient table in FIG. 14, the statistical amounts include a "surge occurrence number" that is the occurrence number of blood pressure surges, and a "mean surge variation amount" a "mean surge peak value", a "mean surge time", a "mean surge rising speed", and a "mean surge falling time" serving as the feature amount of the blood pressure surges. In the patient-by-patient table in FIG. 14, the "surge occurrence number", the "mean surge variation amount", the "mean surge peak value", the "mean surge time", the "mean surge rising speed", the "mean surge rising speed", and the "mean surge falling time" are recorded in association with each other for each patient number for use in identifying a corresponding patient (subject) (for the sake of simplicity, the "mean surge time" is not shown). For example, for a "patient A", the "surge occurrence number" is recorded as 14 times, the "mean surge variation amount" is recorded as 27 mmHg, the "mean surge peak value" is recorded as 149 mmHg, the "mean surge rising speed" is recorded as 1.3 mmHg/sec, and the "mean surge falling time" is recorded as 15 sec. For a "patient C", the "surge occurrence number" is recorded as one time, the "mean surge variation amount" is recorded as 21 mmHg, the "mean surge peak value" is recorded as 149 mmHg, the "mean surge rising speed" is recorded as 0.8 mmHg/sec, and the "mean surge falling time" is recorded as 5 sec. For a "patient E", the "surge occurrence number" is recorded as 25 times, the "mean surge variation amount" is recorded as 31 mmHg, the "mean surge peak value" is recorded as 158 mmHg, the "mean surge rising speed" is recorded as 2.1 mmHg/sec, and the "mean surge falling time" is recorded as 21 sec.

(3) Processing of Obtaining Required Attention Degree (Step S15 in FIG. 13)

Next, in step S15 in FIG. 13, the control part 350 of the server 300 acts as a required attention degree calculation part to obtain a required attention degree (denoted by DC) indicating a level of attention being required to the blood pressure surge for each patient (subject).

In this example, the control part 350 performs processing the same as in step S5 in FIG. 6 for each patient listed in the patient-by-patient table in FIG. 14 to obtain the required attention degree DC based on a result of comparison between the "surge occurrence number", the "mean surge variation amount" and the "mean surge peak value", and respective predetermined thresholds.

That is, first, the control part 350 acts as an individual index calculation part to obtain, for each patient, three individual indexes (corresponding to the "occurrence number index" ID1, the "variation amount index" ID2 and the "peak value index" ID3 described above) each indicating a level of attention being required to a corresponding one of the "surge occurrence number", the "mean surge variation amount" and the "mean surge peak value" shown in the patient-by-patient table in FIG. 14. Next, the control part 350 acts as an integration processing part to obtain, for each patient, the required attention degree DC as one of the three levels (low, medium, high) using the three individual indexes.

The "required attention degree" DC thus obtained is recorded for each patient in the patient-by-patient table in FIG. 14. In this example, the "required attention degree" DC is recorded in association with each patient in the patient-by-patient table in FIG. 14 in such a manner that "medium" is recorded for the "patient A", "medium" is recorded for the "patient B", "low" is recorded for the "patient C", "low" is recorded for the "patient D", "high" is recorded for the "patient E", and "medium" is recorded for the "patient F".

Note that the "surge occurrence number" in the time slot table in FIG. 10 is the occurrence number for each time slot, whereas the "surge occurrence number" in the patient-by-patient table in FIG. 14 is the occurrence number for one night. Therefore, in step S15 in FIG. 13, the thresholds α1, α2 for the "surge occurrence number" are desirably set to be greater than the thresholds α1, α2 for the "surge occurrence number" in step S5 in FIG. 6.

In the above-described example, the three individual indexes including the "occurrence number index" ID1, the "variation amount index" ID2 and the "peak value index" ID3 are used as the individual indexes as in the first blood pressure-related information display method, but the individual indexes are not limited to such three ones. As the individual indexes, in addition to the above-described three individual indexes, the "surge time index", the "surge rising speed index", and the "surge falling time index" may be used. Further, in addition to such individual indexes, individual indexes indicating a level of attention being required to statistical amounts such as a standard deviation, a maximum value and minimum value, and quartiles other than the mean values may be used.

(4) Processing of Displaying Blood Pressure Surge-Related Information (Step S16 in FIG. 13)

Figure 15:
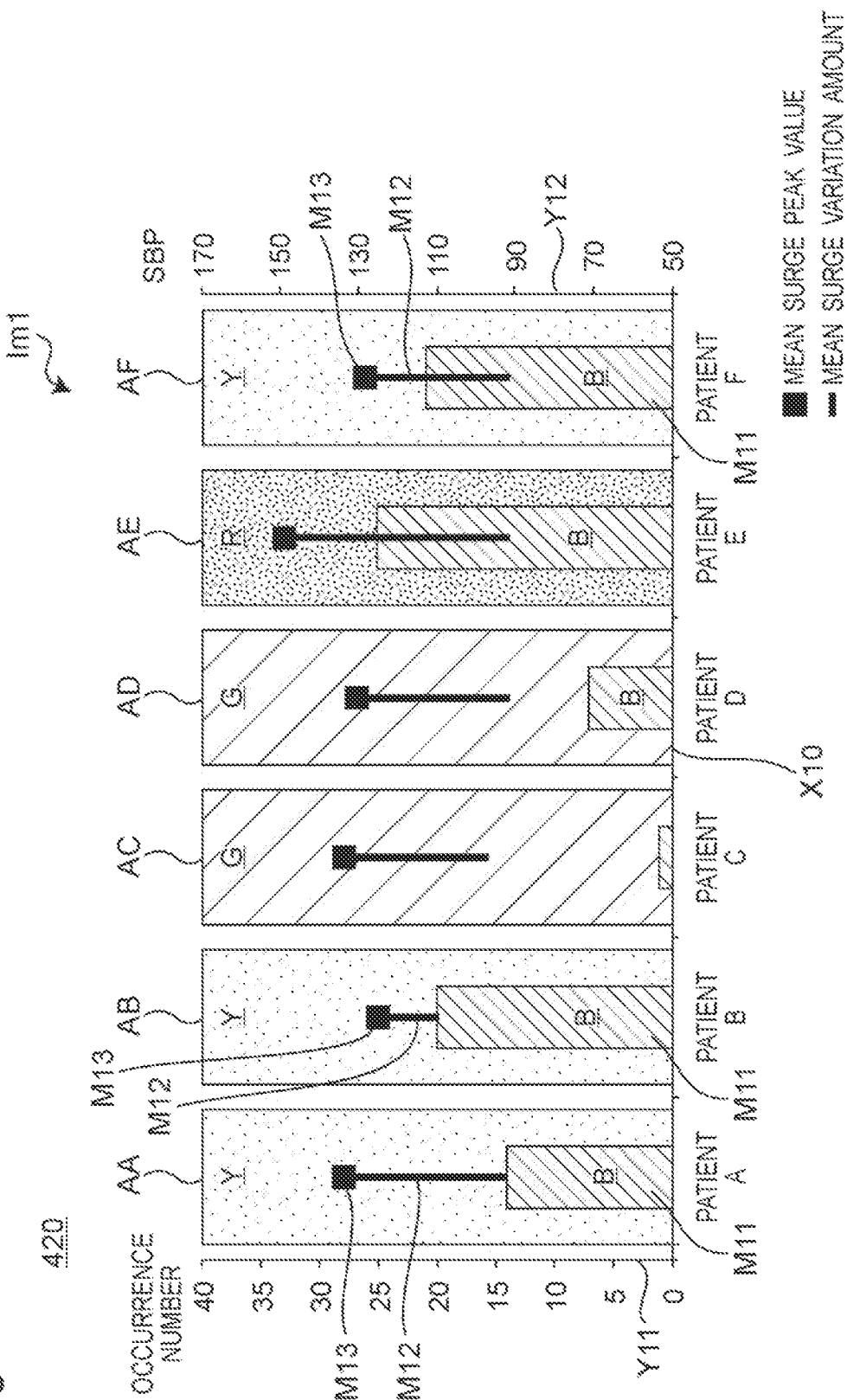
FIG. 15 is a diagram illustrating a display example where the required attention degree obtained and the statistical amounts are displayed side by side for each patient on the display screen.
Figure 16A:
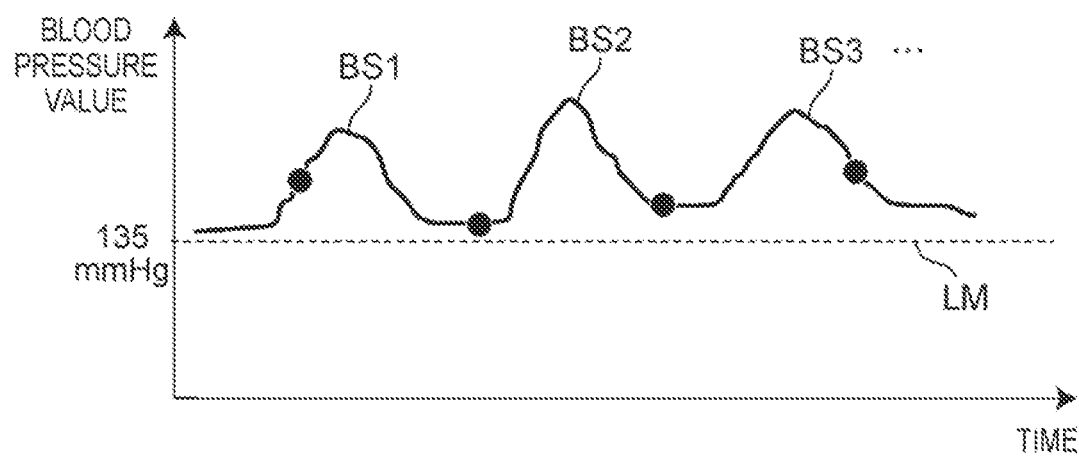
FIG. 16A is a diagram for describing that spot measurement under ABPM cannot observe a blood pressure surge itself sufficiently.
Figure 16B:
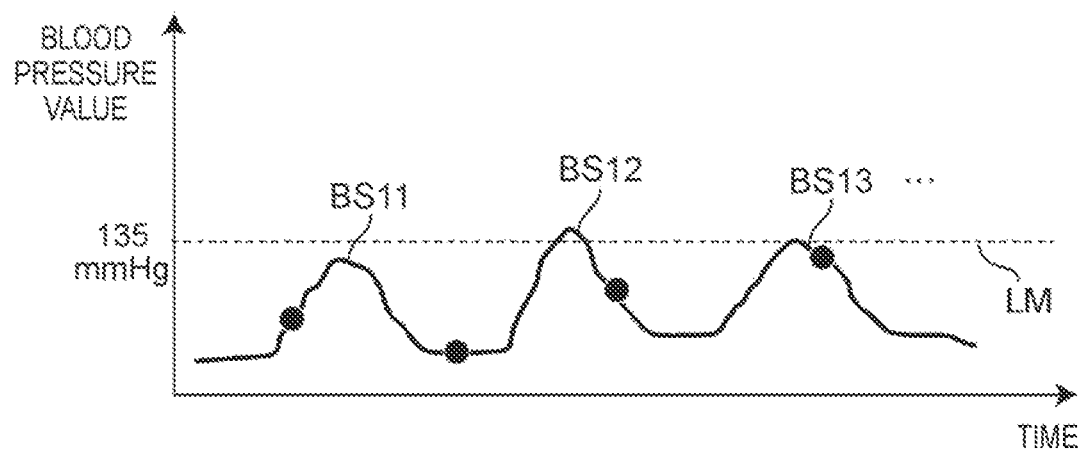
FIG. 16B is a diagram for describing that spot measurement under ABPM cannot observe a blood pressure surge itself sufficiently.

Next, in step S16 in FIG. 13, in this example, the control part 350 of the server 300 creates image data (denoted by Im1) where the required attention degree DC obtained, the "surge occurrence number", the "mean surge variation amount", and the "mean surge peak value" are displayed side by side for each patient (subject). Any of the hospital terminals 400 (400A, 400B, . . . ) receives the image data Im1 from the server 300 over the network 900. The hospital terminal 400 acts as a display processing part to display, in graph form, the image data Im1 on the display screen of the display device 420 as illustrated in FIG. 15.

In this example, the image data Im1 includes rectangular closed areas AA, AB, AC, AD, AE, AF, corresponding to the respective patients A, B, C, D, E, F, . . . set, on the display screen, side by side along the horizontal direction (horizontal axis X10). Each of the closed areas AA, AB, AC, AD, AE, AF, . . . is given a specific color according to the required attention degree DC of a corresponding patient. As the "specific color", in this example, three colors, green (G) corresponding to "low" of the required attention degree DC, yellow (Y) corresponding to "medium" of the required attention degree DC, and red (R) corresponding to "high" of the required attention degree DC, are used as in the first blood pressure-related information display method.

For example, in the patient-by-patient table in FIG. 14, the "required attention degree" DC is recorded as "medium" for the "patient A". Accordingly, in the image data Im1 in FIG. 15, yellow (Y) is applied to the closed area AA. Further, in the patient-by-patient table in FIG. 14, the "required attention degree" DC is recorded as "low" for the "patient C". Accordingly, in the image data Im1 in FIG. 15, green (G) is applied to the closed area AC. Further, in the patient-by-patient table in FIG. 14, the "required attention degree" DC is recorded as "high" for the "patient E". Accordingly, in the image data Im1 in FIG. 15, red (R) is applied to the closed area AE. As described above, in the image data Im1, to each of the closed areas AA, AB, AC, AD, AE, AF, . . . , the specific color according to the required attention degree DC of a corresponding patient is applied.

This allows the user to intuitively grasp the required attention degree DC (that is, a level of attention being required to the blood pressure surge) for each patient by viewing the display screen of the display device 420.

Further, in this example, on the display screen of the display device 420, the image data Im1 is displayed with graphs showing the "surge occurrence number", the "mean surge variation amount", and the "mean surge peak value" for one night superimposed on each of the plurality of closed areas AA, AB, AC, AD, AE, AF, In this example, the "surge occurrence number" is represented as a bar graph M11 for each patient. Blue (B) is applied to each bar forming the bar graph M11. Blue (B) is different from any specific color (green (G), yellow (Y), red (R)) for use in indicating the required attention degree DC, and thus can be easily distinguished from a background color (color of each of the closed areas AA, AB, AC, AD, AE, AF, . . . ). The user can intuitively grasp the "surge occurrence number" for one night by viewing the bar graph M11. Note that, in this example, a scale for the "surge occurrence number" is provided on the left side along a vertical axis Y11.

Further, in this example, the "mean surge peak value" is represented as a square dot-shaped mark M13 for each patient. The dot-shaped mark M13 may be a circle, a triangle, or the like, instead of a square. The "mean surge variation amount" is represented as a line-shaped mark M12 extending downward from each dot-shaped mark M13 representing the "mean surge peak value". A color of the dot-shaped mark M13 and the line-shaped mark M12 may be any color as long as the color can be easily distinguished from the background color (color of each of the closed areas AA, AB, AC, AD, AE, AF, . . . ), and may be, for example, black (Bk). The user can intuitively grasp the "mean surge variation amount" and the "mean surge peak value" for each patient by viewing the marks M12, M13. In this example, a scale for the "mean surge variation amount" and the "mean surge peak value" is provided on the right side along a vertical axis Y12.

Further, the user can intuitively grasp a reason or basis that the required attention degree DC (color of each of the closed areas AA, AB, AC, AD, AE, AF, . . . ) is green (G) (low level), yellow (Y) (medium level), or red (R) (high level) for each patient by viewing the graphs (the bar graph M11 and the marks M12, M13) representing the "surge occurrence number", the "mean surge variation amount", and the "mean surge peak value" for one night.

As described above, under the blood pressure-related information display method, the information on the blood pressure surge is displayed in a visualized form for each patient (subject). This allows the user the grasp the required attention degree DC indicating a level of attention being required to the blood pressure surge and the statistical amounts of the feature amount indicating the characteristics of the blood pressure surge for each patient by viewing the display screen of the display device 420. This allows, for example, a doctor to preferentially evaluate or analyze a condition of a patient having the highest required attention degree DC among the plurality of patients. Further, the doctor can specify patients having similar required attention degrees DC and/or statistical amounts as a group. As a result, for the patients belonging to the group, it is possible to search for common points in lifestyle, common trends in other measurement values (for example, measurement values related to cardiovascular events) other than the blood pressure surge, and the like or to examine differences from the other groups. As described above, it is possible to make effective analysis for diagnosis and treatment of the blood pressure surge.

Note that, in the above-described example, both the required attention degree DC indicating a level of attention being required to the blood pressure surge and the graph (the bar graph M11 and the marks M12, M13) of the statistical amounts of the feature amount indicating the characteristics of the blood pressure surge are displayed side by side for each patient on the display screen of the display device 420, but the present invention is not limited to such a configuration. Only one of the required attention degree DC indicating a level of attention being required to the blood pressure surge or the graph of the statistical amounts of the feature amount indicating the characteristics of the blood pressure surge may be displayed side by side for each patient.

Further, under the second blood pressure-related information display method, the rectangular closed areas AA, AB, AC, AD, AE, AF, . . . corresponding to the respective patients A, B, C, D, E, F, . . . may be displayed, on the display screen, side by side along the vertical direction (vertical axis). In this case, the graph (the bar graph M11 and the marks M12, M13) representing the "surge occurrence number", the "mean surge variation amount", and the "mean surge peak value" for one night for each patient may be superimposed on a corresponding one of the closed areas AA, AB, AC, AD, AE, AF, . . . and displayed in accordance with the scale of the horizontal axis.

(First Modification)

According to the above-described embodiment, the control part 350 of the server 300 creates the image data Im, Im1, and the display device 420 of the hospital terminal 400 displays the image, but the present invention is not limited to such a configuration. The control part 350 of the server 300 may transmit only data for use in image creation instead of transmitting the image data Im, Im1 to the hospital terminal 400, and the hospital terminal 400 may exclusively create the image data Im, Im1

(Second Modification)

Further, according to the above-described embodiment, the blood pressure-related information display device according to the present invention is configured as the system 100 on the network including the hospital terminal 400 and the server 300, but the blood pressure-related information display device is not limited to such a configuration.

For example, the blood pressure-related information display device according to the present invention may include only the hospital terminal 400 (for example, 400A). That is, the hospital terminal 400 may execute all of the blood pressure-related information display method (including processing from reception of the blood pressure time-series data from the sphygmomanometer 200 to display of the image data on the display screen of the display device 420).

In this case, a program for executing the blood pressure-related information display method is installed in the hospital terminal 400. It is thus possible to make the blood pressure-related information display device according to the present invention small in size and compact.

Further, the above-described blood pressure-related information display method may be recorded as software (computer program) on a recording medium capable of storing data in a non-transitory manner such as a compact disc (CD), a digital versatile disc (DVD), or a flash memory. Installing software recorded on such a recording medium into a practical computer device such as a personal computer, a personal digital assistant (PDA), or a smartphone allows the computer device to execute the above-described blood pressure-related information display method.

(Third Modification)

Further, according to the above-described embodiment, the individual indexes (the "occurrence number index" ID1, the "variation amount index" ID2, and the "peak value index" ID3) and the required attention degree DC are obtained as one of the three levels of low, medium, and high, but the present invention is not limited to such a configuration. The number of levels (denoted by m) into which the individual indexes and the required attention degree DC are classified may be equal to two or equal to or greater than four. The smaller the value of m, the simpler the arithmetic processing. On the other hand, the greater the value of m, the higher the accuracy in obtaining the required attention degree DC. Note that, when m is equal to two, the number of thresholds for each individual index may be one. In this case, the level indicated by each individual index has two levels, "low" and "high", for example. Accordingly, the required attention degree DC has two levels, i.e. "low" to which green (G) is applied, and "high" to which red (R) is applied, for example. Further, when m is equal to or greater than four, the number of thresholds for each individual index may be set to (m−1) different in magnitude. In this case, the level indicated by the individual index has m levels (m≥4). Accordingly, the required attention degree DC has, for example, m levels having m specific colors different from each other applied.

(Fourth Modification)

Further, according to the above-described embodiment, the sphygmomanometer 200 is of a tonometry-type, but is not limited to such a type. The sphygmomanometer 200 may include a light emitting element that emits light toward an artery passing through a corresponding portion of the to-be-measured part and a light receiving element that receives reflected light (or transmitted light) of the light and continuously detect blood pressure based on a change in volume of the artery (photoelectric type). Further, the sphygmomanometer 200 may include a piezoelectric sensor in contact with the to-be-measured part, detect distortion due to pressure in the artery passing through the corresponding portion of the to-be-measured part as a change in electric resistance, and continuously detect blood pressure based on the change in electric resistance (piezoelectric type). Furthermore, the sphygmomanometer 200 may include a transmission element that transmits a radio wave (transmission wave) toward the artery passing through the corresponding portion of the to-be-measured part and a reception element that receives a reflected wave of the radio wave, detect a change in distance between the artery and the sensor due to a pulse wave of the artery as a phase shift between the transmission wave and the reflected wave, and continuously detect blood pressure based on the phase shift (radio wave irradiation type). Further, as long as a physical quantity from which blood pressure can be obtained can be observed, different methods may be applied.

As described above, a blood pressure-related information display device according to the present disclosure is a blood pressure-related information display device that displays information on a blood pressure surge in a visualized form, the blood pressure-related information display device comprising:

a blood pressure surge detection part configured to detect, based on predetermined determination criteria, blood pressure surges from time-series data on blood pressure of a subject that varies with pulsation;

a feature amount calculation part configured to obtain a feature amount indicating a characteristic of each blood pressure surge detected;

a statistical amount calculation part configured to perform statistical processing on an occurrence number of the blood pressure surges detected and/or the feature amount to obtain a statistical amount for each of time slots, the statistical amount including at least the occurrence number of the blood pressure surges, a surge variation amount serving as the feature amount, and a surge peak value serving as the feature amount;

a required attention degree calculation part configured to obtain, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the time slots; and a display processing part configured to display, for each of the time slots, the required attention degree obtained and/or the statistical amount side by side on a display screen, wherein the required attention degree calculation part includes, when m is a natural number equal to or greater than two, an individual index calculation part configured to obtain, for each of the time slots, individual indexes indicating a level of attention being required to each statistical amount for the occurrence number of the blood pressure surges, the surge variation amount serving as the feature amount, and the surge peak value serving as the feature amount as one of m levels according to the level of attention being required based on a result of comparison with respective (m−1) predetermined thresholds different in magnitude, and an integration processing part configured to obtain, for each of the time slots, the required attention degree as one of the m levels by using the individual indexes obtained for each of the occurrence number of the blood pressure surges, the surge variation amount serving as the feature amount, and the surge peak value serving as the feature amount.

As used herein, the "predetermined determination criteria" typically refer to criteria for detection of a blood pressure surge of a patient suffering from sleep apnea syndrome (SAS). For example, as disclosed in Japanese Patent Application No. 2017-048946 and Japanese Patent Application No. 2017-050066, the "predetermined determination criteria" refer to that a range from a surge start point to a surge peak point falls within a peak detection section (for example, a period of 15 pulses), that a difference (blood pressure variation) between a systolic blood pressure value at the surge start point and a systolic blood pressure value at the peak point is equal to or greater than 20 mmHg (or 15 mmHg), that a period between the surge start point and the peak point is longer than a period of five pulses, and that a period between the peak point and a surge end point is longer than a period of seven pulses.

Further, the "feature amount" indicating a characteristic of a blood pressure surge refers to, for example, a surge peak value (blood pressure value at the peak point), a surge variation amount (difference in blood pressure value between the start point of the blood pressure surge and the peak point of the blood pressure surge), a surge time (time between the start point of the blood pressure surge and the end point of the blood pressure surge), a surge rising speed (value obtained by dividing the surge variation amount by the time between the start point of the blood pressure surge and the peak point of the blood pressure surge), or the like of the systolic blood pressure.

Further, the "statistical processing" refers to processing of averaging, processing of obtaining a median value, processing of obtaining a standard deviation, or the like.

Further, the "display screen" typically refers to a screen of a display device, but may be, for example, a paper surface output by a printer.

In the blood pressure-related information display device according to the present disclosure, the blood pressure surge detection part detects, based on the predetermined determination criteria, blood pressure surges from the time-series data on blood pressure of a subject that varies with pulsation.

The feature amount calculation part calculates a feature amount indicating a characteristic of each blood pressure surge thus detected. The statistical amount calculation part performs the statistical processing on the occurrence number of the blood pressure surges detected and/or the feature amount to obtain a statistical amount for each of the time slots. Here, the statistical amount includes at least the occurrence number of the blood pressure surges, a surge variation amount serving as the feature amount, and a surge peak value serving as the feature amount. The required attention degree calculation part obtains, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the time slots. When m is a natural number equal to or greater than two, an individual index calculation part included in the required attention degree calculation part obtains, for each of the time slots, an individual index indicating a level of attention being required to the occurrence number of the blood pressure surges (referred to as an "occurrence number index") as one of m levels according to the level of attention being required based on a result of comparison with predetermined (m−1) thresholds. The individual index calculation part further obtains, for each of the time slots, an individual index indicating a level of attention being required to the statistical amount of the surge variation amount serving as the feature amount (referred to as a "variation amount index") as one of the m levels according to the level of attention being required based on a result of comparison with the predetermined (m−1) thresholds. The individual index calculation part further obtains, for each of the time slots, an individual index indicating a level of attention being required to the statistical amount of the surge peak value serving as the feature amount (referred to as a "peak value index") as one of the m levels according to the level of attention being required based on a result of comparison with the predetermined (m−1) thresholds. Next, an integration processing part included in the required attention degree calculation part obtains, for each of the time slots, the required attention degree as one of the m levels by using the individual indexes obtained for each of the occurrence number of the blood pressure surges, the surge variation amount serving as the feature amount, and the surge peak value serving as the feature amount (that is, the occurrence number index, the variation amount index, and the peak value index). This allows the required attention degree to be obtained as one of the m levels by simple arithmetic processing. The display processing part displays, for each of the time slots, the required attention degree obtained and/or the statistical amount side by side on the display screen. As described above, the blood pressure-related information display device displays, in a visualized form, the information on the blood pressure surge for each of the time slots. This allows a user (typically, medical personnel such as a doctor or a nurse, or a system administrator, or may be a subject, and the same applies hereinafter) to grasp changes in the required attention degree and/or the statistical amount for each of the time slots by viewing the display screen. In particular, the user can grasp changes in the occurrence number of the blood pressure surges, the surge variation amount serving as the feature amount, and the surge peak value serving as the feature amount included in the statistical amount among the time slots by viewing the display screen. This allows, for example, a doctor to grasp a tendency of the condition of the patient (subject) for each of the time slots and easily give advice to the patient at the time of consultation. Further, when there is a request for detailed analysis of the waveform of the blood pressure surge, the doctor can first analyze a surge case in a time slot in which the required attention degree is high and thus can make an efficient analysis. Furthermore, the information displayed on the display screen helps to study the relevancy between the blood pressure surge and a cardiovascular event (angina pectoris, myocardial infarction, ischemic heart disease, or the like) in addition to the diagnosis and treatment of SAS, and may lead to new clinical findings.

In the blood pressure-related information display device of one embodiment, each of the m levels of the required attention degree is represented by a corresponding specific color.

Herein, the "m levels" for the required attention degree refer to, for example, three levels of low, medium, and high, but are not limited to such three levels. Examples of the "specific color" include three colors, green (G), yellow (Y), and red (R), but are not limited to such three colors.

In the blood pressure-related information display device according to this embodiment, each of the m levels of the required attention degree is represented by a corresponding specific color. The specific color displayed on the display screen allows the user to intuitively grasp the level of attention being required indicated by the required attention degree.

In the blood pressure-related information display device of one embodiment, the display processing part sets, on the display screen, a closed area corresponding to each of the time slots side by side along progress of the time slots, and applies, to each of closed areas, the specific color according to the required attention degree in a corresponding one of the time slots.

Herein, the "closed area" refers to, for example, a rectangular area, but is not limited to such a rectangular area. Further, the "progress of the time slots" means an order from a previous time slot toward a subsequent time slot on the display screen.

In the blood pressure-related information display device according to this embodiment, the display processing part sets, on the display screen, the closed area corresponding to each of the time slots side by side along the progress of the time slots. At the same time, the display processing part applies, to each of the closed areas, the specific color according to the required attention degree in a corresponding one of the time slots. This allows the user to intuitively grasp changes in the required attention degree among the time slots by viewing the display screen.

In the blood pressure-related information display device of one embodiment, the display processing part displays, on the display screen, a graph showing the statistical amount with the graph superimposed on each of the closed areas.

In the blood pressure-related information display device according to this embodiment, the display processing part displays, on the display screen, the graph showing the statistical amount with the graph superimposed on each of the closed areas. This allows the user to intuitively grasp not only changes in the level indicated by the required attention degree among the time slots but also changes in the statistical amount among the time slots by viewing the display screen. This further allows the user to intuitively grasp a reason or basis of the level of attention being required indicated by the required attention degree for each of the time slots.

In the blood pressure-related information display device of one embodiment, the integration processing part integrates the individual indexes to obtain the required attention degree as one of the m levels.

The "integrates the individual indexes obtained to obtain the required attention degree as one of the m levels" refers to obtaining the required attention degree, for example, when m equals to three, in a way for determining, as the required attention degree, one (level) of the highest frequency among the three levels of "low", "medium", and "high", indicated by the individual indexes (majority rule) or in a way for determining, as the required attention degree, the highest one (level) among the three levels of "low", "medium", and "high" (higher-level priority rule).

In the blood pressure-related information display device of one embodiment, the integration processing part obtains the required attention degree in a way for determining, as the required attention degree, a level of a highest frequency corresponding to the level of attention being required among the m levels indicated by the individual indexes.

In the blood pressure-related information display device according to this embodiment, the integration processing part obtains the required attention degree in a way for determining, as the required attention degree, a level of the highest frequency corresponding to the level of attention being required among the m levels indicated by the individual indexes (majority rule). According to the majority rule, the required attention degree is determined from the viewpoint of providing a representative one (level) among the individual indexes.

In the blood pressure-related information display device of one embodiment, the integration processing part obtains the required attention degree in a way for determining, as the required attention degree, a highest level corresponding to the level of attention being required among the m levels indicated by the individual indexes.

In the blood pressure-related information display device of one embodiment, the integration processing part obtains the required attention degree in a way for determining, as the required attention degree, the highest one (level) among the m levels indicated by the individual indexes (higher-level priority rule). According to the higher-level priority rule, the required attention degree is determined from the viewpoint that any individual index requiring even little higher attention should be pointed out.

The blood pressure-related information display device of one embodiment further comprises an input part for use in setting each of the thresholds in a variable manner.

The blood pressure-related information display device according to this embodiment allows the user to set the thresholds in a variable manner via the input part. This makes it possible to reflect the experience of the user in each of the thresholds (standards) for each statistical amount of the occurrence number of the blood pressure surges, the surge variation amount serving as the feature amount, and the surge peak value serving as the feature amount.

In particular, when the blood pressure-related information display device includes the input part for use in setting each of the (m−1) thresholds different in magnitude in a variable manner, the user can set the (m−1) thresholds different in magnitude via the input part. This makes it possible to reflect the experience of the user in the standard for use in obtaining each individual index as one of the m levels, and accordingly, in the standard for use in obtaining the required attention degree as one of the m levels.

In the blood pressure-related information display device of one embodiment, the display processing part displays, on the display screen, the occurrence number of the blood pressure surges as a bar graph for each of the time slots, displays the statistical amount of the surge peak value as a dot-shaped mark for each of the time slots, and displays the statistical amount of the surge variation amount as a line-shaped mark extending downward from each dot-shaped mark indicating the surge peak value.

The blood pressure-related information display device according to this embodiment allows the user to intuitively grasp changes in the occurrence number of the blood pressure surges, the surge variation amount serving as the feature amount, and the surge peak value serving as the feature amount included in the statistical amounts among the time slots by viewing the display screen.

In another aspect, a blood pressure-related information display method according to the present disclosure is a blood pressure-related information display device method by which information on a blood pressure surge is displayed in a visualized form, the blood pressure-related information display device method comprising steps of:

detecting, based on predetermined determination criteria, blood pressure surges from time-series data on blood pressure of a subject that varies with pulsation;

obtaining a feature amount indicating a characteristic of each blood pressure surge detected;

performing statistical processing on an occurrence number of the blood pressure surges detected and/or the feature amount to obtain a statistical amount for each of time slots, the statistical amount including at least the occurrence number of the blood pressure surges, a surge variation amount serving as the feature amount, and a surge peak value serving as the feature amount;

obtaining, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the time slots; and displaying, for each of the time slots, the required attention degree obtained and/or the statistical amount side by side on a display screen, wherein the step of obtaining a required attention degree includes, when m is a natural number equal to or greater than two, obtaining, for each of the time slots, individual indexes indicating a level of attention being required to each statistical amount for the occurrence number of the blood pressure surges, the surge variation amount serving as the feature amount, and the surge peak value serving as the feature amount as one of m levels according to the level of attention being required based on a result of comparison with respective (m−1) predetermined thresholds different in magnitude, and obtaining, for each of the time slots, the required attention degree as one of the m levels by using the individual indexes obtained for each of the occurrence number of the blood pressure surges, the surge variation amount serving as the feature amount, and the surge peak value serving as the feature amount.

Under the blood pressure-related information display method according to this embodiment, the information on the blood pressure surge is displayed in a visualized form for each of the time slots. This allows the user to intuitively grasp changes in the required attention degree and/or the statistical amount among the time slots by viewing the display screen. In particular, the user can grasp changes in the occurrence number of the blood pressure surges, the surge variation amount serving as the feature amount, and the surge peak value serving as the feature amount included in the statistical amount among the time slots by viewing the display screen. This allows, for example, a doctor to grasp a tendency of the condition of the patient (subject) for each of the time slots and easily give advice to the patient at the time of consultation. Further, when there is a request for detailed analysis of the waveform of the blood pressure surge, the doctor can first analyze a surge case in a time slot in which the required attention degree is high and thus can make an efficient analysis. Furthermore, the information displayed on the display screen helps to study the relevancy between the blood pressure surge and a cardiovascular event (angina pectoris, myocardial infarction, ischemic heart disease, or the like) in addition to the diagnosis and treatment of SAS, and may lead to new clinical findings.

In another aspect, a blood pressure-related information display device that displays information on a blood pressure surge in a visualized form, the blood pressure-related information display device comprising:

a blood pressure surge detection part configured to detect, based on predetermined determination criteria, blood pressure surges from time-series data on blood pressure of a subject that varies with pulsation;

a feature amount calculation part configured to obtain a feature amount indicating a characteristic of each blood pressure surge detected;

a statistical amount calculation part configured to perform statistical processing on an occurrence number of the blood pressure surges detected and/or the feature amount for a plurality of subjects to obtain a statistical amount for each of the subjects, the statistical amount including at least the occurrence number of the blood pressure surges, a surge variation amount serving as the feature amount, and a surge peak value serving as the feature amount;

a required attention degree calculation part configured to obtain, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the subjects; and a display processing part configured to display, for each of the subjects, the required attention degree obtained and/or the statistical amount side by side on a display screen, wherein the required attention degree calculation part includes, when m is a natural number equal to or greater than two, an individual index calculation part configured to obtain, for each of the subjects, individual indexes indicating a level of attention being required to each statistical amount for the occurrence number of the blood pressure surges, the surge variation amount serving as the feature amount, and the surge peak value serving as the feature amount as one of m levels according to the level of attention being required based on a result of comparison with respective (m−1) predetermined thresholds different in magnitude, and an integration processing part configured to obtain, for each of the subjects, the required attention degree as one of the m levels by using the individual indexes obtained for each of the occurrence number of the blood pressure surges, the surge variation amount serving as the feature amount, and the surge peak value serving as the feature amount.

In the blood pressure-related information display device according to the present disclosure, the blood pressure surge detection part detects, based on the predetermined determination criteria, blood pressure surges from the time-series data on blood pressure of a subject that varies with pulsation. The feature amount calculation part calculates a feature amount indicating a characteristic of each blood pressure surge thus detected. The statistical amount calculation part performs the statistical processing on the occurrence number of the blood pressure surges detected and/or the feature amount for the plurality of the subjects to obtain a statistical amount for each of the subjects. Here, the statistical amount includes at least the occurrence number of the blood pressure surges, a surge variation amount serving as the feature amount, and a surge peak value serving as the feature amount. The required attention degree calculation part obtains, based on a result of comparison between each statistical amount for the occurrence number of the blood pressure surges, the surge variation amount serving as the feature amount, and the surge peak value serving as the feature amount, and respective predetermined thresholds, the required attention degree indicating a level of attention being required to the blood pressure surge for each of the subjects. When m is a natural number equal to or greater than two, an individual index calculation part included in the required attention degree calculation part obtains, for each of the subjects, an individual index indicating a level of attention being required to the occurrence number of the blood pressure surges (referred to as an "occurrence number index") as one of m levels according to the level of attention being required based on a result of comparison with predetermined (m−1) thresholds. The individual index calculation part further obtains, for each of the subjects, an individual index indicating a level of attention being required to the statistical amount of the surge variation amount serving as the feature amount (referred to as a "variation amount index") as one of the m levels according to the level of attention being required based on a result of comparison with the predetermined (m−1) thresholds. The individual index calculation part further obtains, for each of the subjects, an individual index indicating a level of attention being required to the statistical amount of the surge peak value serving as the feature amount (referred to as a "peak value index") as one of the m levels according to the level of attention being required based on a result of comparison with the predetermined (m−1) thresholds. Next, an integration processing part included in the required attention degree calculation part obtains, for each of the subjects, the required attention degree as one of the m levels by using the individual indexes obtained for the occurrence number of the blood pressure surges, the surge variation amount serving as the feature amount, and the surge peak value serving as the feature amount (that is, the occurrence number index, the variation amount index, and the peak value index). This allows the required attention degree to be obtained as one of the m levels by simple arithmetic processing. The display processing part displays, for each of the subjects, the required attention degree obtained and/or the statistical amounts side by side on the display screen. As described above, the blood pressure-related information display device displays, in a visualized form, the information on the blood pressure surge for each of the subjects. This allows the user to intuitively grasp the required attention degree and/or the statistical amount for each of the subjects by viewing the display screen. In particular, the user can grasp the occurrence number of the blood pressure surges, the surge variation amount serving as the feature amount, and the surge peak value serving as the feature amount included in the statistical amount for each of the subjects by viewing the display screen. This allows, for example, a doctor to preferentially evaluate or analyze a condition of a patient having the highest required attention degree among a plurality of patients (subjects). Further, the doctor can specify patients having similar required attention degrees and/or statistical amounts as a group. As a result, for the patients belonging to the group, it is possible to search for common points in lifestyle, common trends in other measurement values (for example, measurement values related to cardiovascular events) other than the blood pressure surge, and the like or to examine differences from the other groups. As described above, it is possible to make effective analysis for diagnosis and treatment of the blood pressure surge.

In the blood pressure-related information display device of one embodiment, each of the m levels of the required attention degree is represented by a corresponding specific color.

In the blood pressure-related information display device according to this embodiment, each of the m levels of the required attention degree is represented by a corresponding specific color. The specific color displayed on the display screen allows the user to intuitively grasp the level of attention being required indicated by the required attention degree.

In the blood pressure-related information display device of one embodiment, the display processing part sets, on the display screen, a closed area corresponding to each of the subjects side by side along a horizontal direction or vertical direction and applies, to each of closed areas, the specific color according to the required attention degree of a corresponding one of the subjects.

In the blood pressure-related information display device according to this embodiment, the display processing part sets, on the display screen, the closed area corresponding to each of the subjects side by side along the horizontal direction or vertical direction. At the same time, the display processing part applies, to each of the closed areas, the specific color according to the required attention degree of a corresponding one of the subjects. This allows the user to intuitively grasp the required attention degree for each of the subjects by viewing the display screen.

In the blood pressure-related information display device of one embodiment, the display processing part displays, on the display screen, a graph showing the statistical amount with the graph superimposed on each of the closed areas.

In another aspect, a blood pressure-related information display method according to the present disclosure is a blood pressure-related information display method by which information on a blood pressure surge is displayed in a visualized form, the blood pressure-related information display method comprising steps of:

detecting, based on predetermined determination criteria, blood pressure surges from time-series data on blood pressure of a subject that varies with pulsation;

obtaining a feature amount indicating a characteristic of each blood pressure surge detected;

performing statistical processing on an occurrence number of the blood pressure surges detected and/or the feature amount for a plurality of subjects to obtain a statistical amount for each of the subjects, the statistical amount including at least the occurrence number of the blood pressure surges, a surge variation amount serving as the feature amount, and a surge peak value serving as the feature amount;

obtaining, based on a result of comparison between each statistical amount for the occurrence number of the blood pressure surges, the surge variation amount serving as the feature amount, and the surge peak value serving as the feature amount, and respective predetermined thresholds, a required attention degree indicating a level of attention being required to the blood pressure surge for each of the subjects; and displaying, for each of the subjects, the required attention degree obtained and/or the statistical amount side by side on a display screen, wherein the step of obtaining a required attention degree includes, when m is a natural number equal to or greater than two, obtaining, for each of the subjects, individual indexes indicating a level of attention being required to each statistical amount for the occurrence number of the blood pressure surges, the surge variation amount serving as the feature amount, and the surge peak value serving as the feature amount as one of m levels according to the level of attention being required based on a result of comparison with respective (m−1) predetermined thresholds different in magnitude, and obtaining, for each of the subjects, the required attention degree as one of the m levels by using the individual indexes obtained for each of the occurrence number of the blood pressure surges, the surge variation amount serving as the feature amount, and the surge peak value serving as the feature amount.

Under the blood pressure-related information display method according to this embodiment, the information on the blood pressure surge is displayed in a visualized form for each of the subjects. This allows the user to intuitively grasp the required attention degree and/or the statistical amounts for each of the subjects by viewing the display screen. In particular, the user can grasp the occurrence number of the blood pressure surges, the surge variation amount serving as the feature amount, and the surge peak value serving as the feature amount included in the statistical amount for each of the subjects by viewing the display screen. This allows, for example, a doctor to preferentially evaluate or analyze a condition of a patient having the highest required attention degree among a plurality of patients (subjects). Further, the doctor can specify patients having similar required attention degrees and/or statistical amounts as a group. As a result, for the patients belonging to the group, it is possible to search for common points in lifestyle, common trends in other measurement values (for example, measurement values related to cardiovascular events) other than the blood pressure surge, and the like or to examine differences from the other groups. As described above, it is possible to make effective analysis for diagnosis and treatment of the blood pressure surge.

In yet another aspect, a computer-readable recording medium according to the present disclosure is a computer-readable recording medium non-transitorily storing a program for causing a computer to execute the above blood pressure-related information display method.

By making a computer read the program stored in the computer-readable recording medium according to the present disclosure and causing a computer to execute the program, the blood pressure-related information display method can be implemented.

As is apparent from the above, according to the blood pressure-related information display device and the blood pressure-related information display method according to the present disclosure, the information on the blood pressure surge can be displayed in a visualized form for each of the time slots. Further, when the computer executes the program stored in the computer-readable recording medium according to the present disclosure, the blood pressure-related information display method can be implemented.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A blood pressure-related information display device that displays information on a blood pressure surge in a visualized form, the blood pressure-related information display device comprising:
a processor programmed to act as
a blood pressure surge detection part to detect, based on predetermined determination criteria, blood pressure surges from time-series blood pressure data of a subject that varies with pulsation;
a feature amount calculation part to obtain a feature amount indicating a characteristic of each blood pressure surge detected, wherein the feature amount includes at least a surge variation amount and a surge peak value;
a statistical amount calculation part to perform statistical processing on an occurrence number of the blood pressure surges detected and the feature amount to obtain a statistical amount for each of a plurality of time slots, the statistical amount including at least the occurrence number of the blood pressure surges, a surge variation amount statistic and a surge peak value statistic;
a required attention degree calculation part to obtain, based on a result of comparison for the occurrence number of the blood pressure surges, the surge variation amount statistic and the surge peak value statistic included in the statistical amount with respective predetermined thresholds, a required attention degree indicating a level of attention being required to the blood pressure surge for each of the time slots; and
a display processing part to display, for each of the time slots, the required attention degree obtained and the statistical amount on a display screen, wherein
the required attention degree calculation part is configured to act as, when m is a natural number equal to or greater than two,
an individual index calculation part to obtain, for each of the time slots, individual indexes respectively indicating a level of attention being required for the occurrence number of the blood pressure surges, the surge variation amount statistic and the surge peak value statistic as one of m levels according to the level of attention being required based on a result of comparison with respective (m−1) predetermined thresholds different in magnitude, and
an integration processing part to obtain, for each of the time slots, the required attention degree as one of the m levels by using the individual indexes respectively obtained for the occurrence number of the blood pressure surges, the surge variation amount statistic and the surge peak value statistic, wherein the programmed processor acting as the display processing part is configured to
set, on the display screen, a plurality of closed areas respectively corresponding to the time slots side by side along progress of the time slots,
apply, to each of the closed areas, a specific color according to the level of the required attention degree in a corresponding one of the time slots, and
display, on the display screen, a graph showing the statistical amount with the graph superimposed on each of the closed areas, such that the required attention degree and the statistical amount obtained for a first time slot is displayed side by side with the required attention degree and the statistical amount obtained for a second time slot.

2. The blood pressure-related information display device according to claim 1, wherein
the programmed processor acting as the integration processing part is configured to integrate the individual indexes to obtain the required attention degree as one of the m levels.

3. The blood pressure-related information display device according to claim 2, wherein
the programmed processor acting as the integration processing part is configured to obtain the required attention degree in a way for determining, as the required attention degree, a level of a highest frequency corresponding to the level of attention being required among the m levels indicated by the individual indexes.

4. The blood pressure-related information display device according to claim 2, wherein
the programmed processor acting as the integration processing part is configured to obtain the required attention degree in a way for determining, as the required attention degree, a highest level corresponding to the level of attention being required among the m levels indicated by the individual indexes.

5. The blood pressure-related information display device according to claim 1, further comprising a mouse, keyboard, or touchscreen display for setting each of the thresholds in a variable manner.

6. The blood pressure-related information display device according to claim 1, wherein
the programmed processor acting as the display processing part is configured to display, on the display screen, the occurrence number of the blood pressure surges as a bar graph for each of the time slots, display the surge peak value statistic as a dot-shaped mark for each of the time slots, and display the surge variation amount statistic as a line-shaped mark extending downward from each dot-shaped mark indicating the surge peak value statistic.

7. A blood pressure-related information display method by which information on a blood pressure surge is displayed in a visualized form, the blood pressure-related information display method comprising steps of, by a programmed processor:
detecting, based on predetermined determination criteria, blood pressure surges from time-series blood pressure data of a subject that varies with pulsation;
obtaining a feature amount indicating a characteristic of each blood pressure surge detected, wherein the feature amount includes at least a surge variation amount and a surge peak value;
performing statistical processing on an occurrence number of the blood pressure surges detected and the feature amount to obtain a statistical amount for each of a plurality of time slots, the statistical amount including at least the occurrence number of the blood pressure surges, a surge variation amount statistic and a surge peak value statistic;

obtaining, based on a result of comparison for the occurrence number of the blood pressure surges, the surge variation amount statistic and the surge peak value statistic included in the statistical amount with respective predetermined thresholds, a required attention degree indicating a level of attention being required to the blood pressure surge for each of the time slots; and displaying, for each of the time slots, the required attention degree obtained and the statistical amount on a display screen, wherein the step of obtaining a required attention degree includes, when m is a natural number equal to or greater than two, obtaining, for each of the time slots, individual indexes respectively indicating a level of attention being required for the occurrence number of the blood pressure surges, the surge variation amount statistic and the surge peak value statistic as one of m levels according to the level of attention being required based on a result of comparison with respective (m−1) predetermined thresholds different in magnitude, and obtaining, for each of the time slots, the required attention degree as one of the m levels by using the individual indexes respectively obtained for the occurrence number of the blood pressure surges, the surge variation amount statistic and the surge peak value statistic, wherein the step of displaying includes
setting, on the display screen, a plurality of closed areas respectively corresponding to the time slots side by side along progress of the time slots,
applying, to each of the closed areas, a specific color according to the level of the required attention degree obtained for corresponding one of the time slots, and
displaying, on the display screen, a graph showing the statistical amount with the graph superimposed on each of the closed areas, such that the required attention degree and the statistical amount obtained for a first time slot is displayed side by side with the required attention degree and the statistical amount obtained for a second time slot adjacent to the first time slot.

8. A computer-readable recording medium non-transitorily storing a program for causing a computer to execute a blood pressure-related information display method according to claim 7.

9. A blood pressure-related information display device that displays information on a blood pressure surge in a visualized form, the blood pressure-related information display device comprising:

a processor programmed to act as
a blood pressure surge detection part to detect for each of a plurality of subjects, blood pressure surges from time-series blood pressure data that varies with pulsation of the subject, based on predetermined determination criteria;
a feature amount calculation part to obtain, for each of the subjects, a feature amount indicating a characteristic of each blood pressure surge detected within the respective time-series blood pressure data, wherein the feature amount comprises at least a surge variation amount and a surge peak value;

a statistical amount calculation part to perform, for each of the subjects, statistical processing on an occurrence number of the blood pressure surges detected within the respective time-series blood pressure data and the respective feature amounts to obtain a statistical amount for each of the subjects, the statistical amount including at least the occurrence number of the blood pressure surges, a surge variation amount statistic and a surge peak value statistic;

a required attention degree calculation part to obtain, based on a result of comparison for the occurrence number of the blood pressure surges, the surge variation amount statistic and the surge peak value statistic included in the statistical amount with respective predetermined thresholds, a required attention degree indicating a level of attention being required to the blood pressure surge for each of the subjects; and a display processing part to display, for each of the subjects, the required attention degree obtained and the statistical amount on a display screen, wherein the programmed processor acting as the required attention degree calculation part is configured to act as, when m is a natural number equal to or greater than two, an individual index calculation part to obtain, for each of the subjects, individual indexes respectively indicating a level of attention being required for the occurrence number of the blood pressure surges, the surge variation amount statistic and the surge peak value statistic as one of m levels according to the level of attention being required based on a result of comparison with respective (m−1) predetermined thresholds different in magnitude, and an integration processing part to obtain, for each of the subjects, the required attention degree as one of the m levels by using the individual indexes respectively obtained for the occurrence number of the blood pressure surges, the surge variation amount statistic and the surge peak value statistic, wherein the programmed processor acting as the display processing part is configured to set, on the display screen, a plurality of closed areas respectively corresponding to the subjects side by side along a horizontal direction or vertical direction,
apply, to each of the closed areas, a specific color according to the level of the required attention degree of a corresponding one of the subjects, and
display, on the display screen, a graph showing the statistical amount with the graph superimposed on each of the closed areas, such that the required attention degree and the statistical amount obtained for a first subject is displayed side by side with the required attention degree and the statistical amount obtained for a second subject.

10. A blood pressure-related information display method by which information on a blood pressure surge is displayed in a visualized form, the blood pressure-related information display method comprising steps of, by a programmed processor:

detecting, for each of a plurality of subjects, blood pressure surges from time-series blood pressure data that varies with pulsation of the subject, based on predetermined determination criteria;
obtaining, for each of the subjects, a feature amount indicating a characteristic of each blood pressure surge detected within the respective time-series blood pressure data, wherein the feature amount comprises at least a surge variation amount and a surge peak value;

performing, for each of the subjects, statistical processing on an occurrence number of the blood pressure surges detected within the respective time-series blood pressure data and the respective feature amounts to obtain a statistical amount for each of the subjects, the statistical amount including at least the occurrence number of the blood pressure surges, a surge variation amount statistic and a surge peak value statistic;

obtaining, based on a result of comparison for the occurrence number of the blood pressure surges, the surge variation amount statistic and the surge peak value statistic included in the statistical amount with respective predetermined thresholds, a required attention degree indicating a level of attention being required to the blood pressure surge for each of the subjects; and displaying, for each of the subjects, the required attention degree obtained and the statistical amount on a display screen, wherein the step of obtaining a required attention degree includes, when m is a natural number equal to or greater than two, obtaining, for each of the subjects, individual indexes respectively indicating a level of attention being required for the occurrence number of the blood pressure surges, the surge variation amount statistic and the surge peak value statistic as one of m levels according to the level of attention being required based on a result of comparison with respective (m−1) predetermined thresholds different in magnitude, and obtaining, for each of the subjects, the required attention degree as one of the m levels by using the individual indexes respectively obtained for the occurrence number of the blood pressure surges, the surge variation amount statistic and the surge peak value statistic, wherein the step of displaying includes setting, on the display screen, a plurality of closed areas respectively corresponding to the subjects side by side along a horizontal direction or vertical direction, applying, to each of the closed areas, a specific color according to the level of the required attention degree of a corresponding one of the subjects, and displaying, on the display screen, a graph showing the statistical amount with the graph superimposed on each of the closed areas, such that the required attention degree and the statistical amount obtained for a first subject is displayed side by side with the required attention degree and the statistical amount obtained for a second subject.

11. A computer-readable recording medium non-transitorily storing a program for causing a computer to execute a blood pressure-related information display method according to claim 10.

* * * * *